(12) United States Patent
Barritault et al.

(10) Patent No.: US 8,883,715 B2
(45) Date of Patent: Nov. 11, 2014

(54) BIOCOMPATIBLE POLYMERS, PROCESS FOR THEIR PREPARATION AND COMPOSITIONS CONTAINING THEM

(71) Applicants: Denis Barritault, Paris (FR); Jean-Pierre Caruelle, Saint-Maur-des-Fosses (FR)

(72) Inventors: Denis Barritault, Paris (FR); Jean-Pierre Caruelle, Saint-Maur-des-Fosses (FR)

( * ) Notice: Subject to any disclaimer, the term of this patent is extended or adjusted under 35 U.S.C. 154(b) by 0 days.

(21) Appl. No.: 13/861,898

(22) Filed: Apr. 12, 2013

(65) Prior Publication Data

US 2013/0287725 A1   Oct. 31, 2013

Related U.S. Application Data

(60) Division of application No. 13/160,099, filed on Jun. 14, 2011, now Pat. No. 8,476,220, which is a continuation of application No. 12/212,093, filed on Sep. 17, 2008, now abandoned, which is a continuation of application No. 10/695,574, filed on Oct. 28, 2003, now Pat. No. 7,998,922, which is a division of application No. 09/765,788, filed on Jan. 19, 2001, now Pat. No. 6,689,741, which is a continuation of application No. PCT/FR99/01774, filed on Jul. 20, 1999.

(30) Foreign Application Priority Data

Jul. 21, 1998   (FR) ...................................... 98 09309

(51) Int. Cl.
| | | |
|---|---|---|
| *A61K 31/00* | (2006.01) | |
| *C08G 63/688* | (2006.01) | |
| *A61K 31/795* | (2006.01) | |
| *A61K 31/765* | (2006.01) | |
| *A61K 31/721* | (2006.01) | |
| *C08B 37/02* | (2006.01) | |

(52) U.S. Cl.
CPC .......... *A61K 31/795* (2013.01); *C08G 63/6882* (2013.01); *A61K 31/765* (2013.01); *A61K 31/721* (2013.01); *C08B 37/0021* (2013.01)
USPC ........ 514/1; 514/53; 514/54; 514/56; 514/59; 435/375

(58) Field of Classification Search
None
See application file for complete search history.

(56) References Cited

U.S. PATENT DOCUMENTS

| | | | |
|---|---|---|---|
| 3,762,924 A | 10/1973 | Morii et al. | |
| 3,907,755 A | 9/1975 | Margraff et al. | |
| 4,740,594 A | 4/1988 | Mauzac et al. | |
| 4,755,379 A | 7/1988 | Jozefonvicz et al. | |
| 4,879,282 A * | 11/1989 | Saliba, Jr. .................. 514/56 |
| 4,931,553 A | 6/1990 | Gill et al. | |
| 4,935,338 A | 6/1990 | Masuda et al. | |
| 5,314,881 A | 5/1994 | Rapisarda | |
| 5,691,625 A | 11/1997 | Kumar et al. | |
| 5,693,625 A | 12/1997 | Barritault et al. | |
| 5,852,003 A | 12/1998 | Barritault et al. | |
| 5,852,004 A | 12/1998 | Barritault et al. | |
| 6,517,824 B1 | 2/2003 | Kohn et al. | |
| 6,573,251 B2 | 6/2003 | Barritault et al. | |
| 2004/0131583 A1 | 7/2004 | Barritault et al. | |

FOREIGN PATENT DOCUMENTS

| | | |
|---|---|---|
| CA | 1 231 334 | 1/1988 |
| DE | 25 156 | 3/1959 |
| DE | 1 152 396 | 8/1963 |
| DE | 1152 396 | 8/1963 |
| DE | 62 514 | 4/1967 |
| DE | 1 572 267 | 1/1971 |
| DE | 25 156 | 1/1984 |
| EP | 0 066 283 | 12/1982 |
| EP | 0 168 277 A1 | 1/1986 |
| EP | 0 450 398 | 10/1991 |
| EP | 0 557 887 | 9/1993 |
| FR | 894508 | 12/1944 |
| FR | 2 461 724 | 2/1981 |
| FR | 2 644 066 | 9/1990 |
| FR | 2 718 023 | 10/1995 |
| FR | 2 718 024 | 10/1995 |
| FR | 2 718 026 | 10/1995 |
| FR | R2 718 025 | 10/1995 |
| GA | 894.508 | 12/1944 |
| JP | 49-48785 | 11/1974 |
| JP | 61-9431 | 1/1986 |

(Continued)

OTHER PUBLICATIONS

Catherine Alexakis et al., "Regulation of the Collagen Phenotype Expression of Gamma-Irradiated Vascular Smooth Muscle Cells by Heparin Mimetics (RGTA)," Wiley Periodicals, Inc., 2004, pp. 594-602, J. Biomed. Mater. Res. 70A: 594-602.

Catherine Alexakis et al., "Reversal of Abnormal Collagen Production in Chron's Disease Intesyinal Biopsies Treated with Regenerating Agents," Gut. 2004. 53: 85-90.

Catherine Alexakis et al., "Heparan Mimetic Regulates Collagen Expression and TGF-β1 Distribution in Gamma-Irradiated Human Intestinal Smooth Muscle Cells," The FASEB Journal, 2001, vol. 15, pp. 1546-1554.

(Continued)

*Primary Examiner* — Allison Ford
*Assistant Examiner* — Susan E Fernandez

(57) ABSTRACT

A process for treating fibroses including administering a therapeutically effective amount of a pharmaceutical composition which includes at least one biocompatible polymer of the following general formula (I): $A_aX_xY_y$ wherein: A represents a monomer selected from the group consisting of a sugar or —(O—$CH_2$—$CH_2$—CO)—, X represents a carboxyl group bonded to monomer A, Y represents a sulfate or sulfonate group bonded to monomer A a represents the number of monomers A such that the mass of the polymers of formula (I) is greater than approximately 5,000 da, x represents a substitution rate of the monomers A by the groups X, which is between approximately 20 and 150%, and y represents a substitution rate of the monomers A by the groups Y, which is between approximately 30 and 150%.

15 Claims, 30 Drawing Sheets

(56) References Cited

FOREIGN PATENT DOCUMENTS

| JP | 2-231075 | 9/1990 |
|---|---|---|
| JP | 5-313295 | 11/1993 |
| JP | 2000-516971 | 1/1998 |
| JP | 10-501568 | 2/1998 |
| JP | 2000-516211 | 12/2000 |
| RU | 328094 A | 5/1970 |
| WO | WO 95/26739 | 10/1995 |
| WO | WO 95/34595 | 12/1995 |
| WO | WO 98/03572 | 1/1998 |
| WO | WO 98/03573 | 1/1998 |

OTHER PUBLICATIONS

Emmanuel Petit et al., "Control Sulfatation of Natural Anionic Bacterial Polysaccharides Can Yield Agents with Specific Regenerating Activity in Vivo, Biomacromolecules," Jul. 25, 2003, 8 pages.
Hidetoshi Yamauchi et al., "New Agents for the Treatment of Infracted Myocardium," The FASEB Journal, Sep. 8, 2000, 14 pages.
Patricia Mestries et al., "Specific RGTA Increases Collagen V Expression by Cultured Aortic Smooth Muscle Cells Via Activation and Protection of Transforming Growth Factor-β1," Matrix Biology, 2001, pp. 171-181, Volume 20.
Pascal Desgranges et al., "A Substituted Dextran Enhances Muscle Fiber Survival and Regeneration in Ischemic and Denervated Rat EDL Muscle," The FASEB Journal, 1999, pp. 761-766.
Catherine Alexakis et al., "Structurally Different RGTAs Modulate Collagen—Type Expression by Cultured Aortic Smooth Muscle Cells Via Different Pathways Involving Fibroblast Growth Factor-2 or Transforming Growth Factor-β1," The FASEB Journal, 2004.
Viviane Jeanbat-Mimaud et al., "Bioactive Functionalized Polymer of Malic Acid for Bone Repair and Muscle Regeneration," J. Biomater. Sci. Polymer Edn., 2000, vol. 11, No. 9, pp. 979-991.
K.W. Walton et al., "The Histochemical Basis of Metachromasia," Brit. J. Exptl. Pathol., 1954, pp. 227-240.
C.H. Rückardt et al., "Pathological and Anatomical Findings After Administration of Dextran Sulfate and Carboxymethyl Dextran Sulfates in Experimental Animals," Acta Biol. Med. Ger., 1963, vol. 10, pp. 126-146.
F. Gensicke et al., "Microdistribution of Radio Sulfur in Rabbits After Intravenous Injection of 35S-Labled Dextran and Carboxymethyl Dextran Sulfates," Acta Biol. Med. Ger., 1965, vol. 14, Nos. 3-4 pp. 409-416.
Susumu Sasaki, "Production of Lymophocytosis by Polysaccharide Polysulphates (Heparinoids)," Nature, 1967, vol. 214, pp. 1041-1042.
G. Baggi et al., Influence of Chondroitin Sulfate on the Process of Cicatrization of Experimentally Produced Cutaneous Injuries, Minerva Chirurgica, 1970, vol. 25 (3), pp. 181-184.
Bruce Alberts et al., "Molecular Biology of the Cell," Garland Publishing, Inc., New York, 1983, p. 703.
Didier Letourneur et al., "In Vitro Stimulation of Human Endothelial Cells by Derivatized Dextrans," in Vitro Cell. Dev. Biol.:Anim, 1993, vol. 29A (1), pp. 67-72.
Didier Letourneur et al., "Antiproliferative Capacity of Synthetic Dextrans on Smooth Muscle Cell Growth: TheModel of Derivatized Dextrans as Heparin-Like Polymers," 1993, J. Biomater. Sci. Polym. Ed., vol. 4 (5), pp. 431-444.
Marie-Agnes Leboucher-Durand et al., "Poly(β-malic acid) Derivatives with Unsaturated Lateral Groups: Epoxidation as Model Reaction of the Double Bonds Reactivity," Reactive & Functional Polymers, 1996, vol. 31, No. 1, pp. 57-65.
O. Maiga-Revel et al., "New Investigations on Heparin-Like Derivatized Dextrans: CMDBS, Synergistic Role of Benzylamide and Sulfate Substituents in Anticoagulant Activity," Carbohydrate Polymers, 1997, vol. 32, No. 2, pp. 89-93.
Alt, K. W. et al., "Evidence for Stone Age Cranial Surgery" Nature, May 22, 1997, vol. 387, p. 360.
Biggs, R. et al., "Human Blood Coagulation Haemostasis and Thrombosis" Blackwells, 1984, 3rd edition, p. 601.

Blanquaert, F. et al., "Heparan-Like Molecules Induce the Repair of Skull Defects," Bone, Dec. 1995, vol. 17, No. 6, pp. 499-506.
Bostantjopoulou, S. et al., "Superoxide Dismutase Activity in Early and Advanced Parkinson's Disease," Funct. Neurol., Mar.-Apr. 1997, vol. 12, No. 2, pp. 63-68.
D'Agnillo, F. et al., "Reduction of Hydoxyl Radical Generation in a Rat Hindlimb Model of Ischemia-Reperfusion Injury Using Crosslinked Hemoglobin-Supeoxide Dismutase-Catalase," Artif. Cells Blood Substiti. Immobil. Biotechnol, Jan.-Mar. 1997, vol. 25, Nos. 1-2, pp. 163-180.
Fernandez-Novoa, L. et al., "Effects of Anapsos on the Activity of the Enzyme Cu-Zn-superoxide Dismutase in an Animal Model of Neuronal Degeneration," Methods Find Exp. Clin. Pharmacol., Mar. 1997, vol. 19, No. 2, pp. 99-106.
Freund, M. et al., "The Mechanism of Action of Lymphokines—IX. The Enzymatic Basis of Hydrogen Peroxide Production by Lymphokine-Activated Macrophages," The Journal of Immunology, Aug. 15, 1986, vol. 137, No. 4, pp. 1312-1318.
Guerin, P. et al., "Optically Active Poly. (β-Malic-Acid)," Polymer Bulletin, 1985, vol. 14; pp. 187-192.
Hansen-Smith, F. M. et al., "Revascularization of the Freely Grafted Extensor Digitorum Longus Muscle in the Rat," American Journal of Anatomy, 1980, vol. 158, pp. 65-82.
Ishai-Michaeli, R. et al, Importance of Size and Sulfation of Heparin in Release of Basic Fibroblast Growth Factor from the Vascular Endothelium and Extracellular Matrix, Biochemistry, 1992; vol. 31, pp. 2080-2088 (first page only).
Jun, T, et al., "Increased Superoxide Anion Production in Humans, a Possible Mechanism for the Pathogenesis of Hypertension," Journal of Human Hypertension, 1996, vol. 10, No. 5, pp. 305-310.
Kandasamy, S. B. et al,. "Involvement of Superoxide Dismutase. and Gluthathione Peroxidase in Attenuation of Radiation-Induced Hyperthermia by Interleukin-1α in Rats," Brain Research, 1993, vol. 606, No. 1, pp. 106-110.
Koch, F. H. et al., "Effects of Different Antioxidants on Lens-Induced Uveitis;" Ger. J. Ophthalmol., Jul. 1996, vol. 5, No. 4, pp. 1185-1188.
Laemmli, U.K, "Cleavage of Structural Proteins during Assembly of the Head of Bacteriophage T4," Nature, Aug. 15, 1970, vol. 227, pp. 680-685.
Markgraf, C. G . et al., Six-Hour Window of Opportunity for Calpain Inhibition in Focal Cerebral Ischemia in Rats, Stroke, 1998, vol. 29, pp. 152-158.
Mauzac, M. et al., "Anticoagulant Activity of Dextram Derivatives Part I: Synthesis and Characterization," Biomaterials, Sep. 1984, vol. 5, pp. 301-304.
Meddahi, A. et al., Inhibition by Dextran Derivatives of FGF-2 Plasmin-Mediated Degradation, Biochimie, 1995, vol. 77, pp. 703-706.
Nakauchi, K. et al., "Effects of Lecithinized Superoxide Dismutase on Rat Spinal Cord Injury, J. Neurotrauma," Oct. 1996, vol. 13, No. 10 pp. 573-582.
Oguni, M. et al., "Chronic Retinal Effects by Ultraviolet Irradiation with Special Reference to Superoxide Dismutase," Histol. Histopathol., Jul. 1996, vol. 11, No. 3, pp. 695-702.
Portolés, M. T. et al., "Hepatic Response to the Oxidative Stress Induced by E. coli Endotoxin Glutathione as an Index of the Acute Phase during the Endotoxic Shock," Molecular and Cellular Biochemistry, 1996, vol. 159, pp. 115-121.
Razack, S. et al., "Crosslinked Hemoglobin-Superoxide Dismutase-Catalase Scavenges Free Radicals in a Rat Model of Intestinal Ischernia-Reperfusion Injury," Artificial Cells, Blood Substitutes, and Immobilization Biotechnology, 1997, vol. 25, Nos. 1-2, pp. 181-192.
Rojkind, M. et al., "An Improved Method for Determining Specific Radioactivities of Proline-14C and Hydroxyproline-14C in Collagen and in Noncollagenous Proteins," Analytical Biochemistry, Jan. 1974; vol. 57, issue 1, pp. 1-7.
Saido, T. C. et al., "Up- and Down-Regulation of Calpain Inhibitor Polypeptide, Calpastatin, in Postischemie Hippocampus,"Neuroscience Letters, 1997, vol. 227, pp. 75-78.
Sanchiz, F. et al., "Prevention of Radioinduced Cystitis by Orgotein; a Randomized Study," Anticancer Res., Jul.-Aug. 1996, vol. 16, No. 4A, pp. 2025-2028.

(56) References Cited

OTHER PUBLICATIONS

Sasaki, T. et al., "Comparative Specificity and Kinetic Studies on Porcine Calpain I and Calpain II with Naturally Occurring Peptides and Synthetic Fluorogenic Substrates," The Journal of Immunology, Oct. 25, 1984, vol. 259, No. 20, pp. 12489-12494.

Sethi, N. C. et al., "Serum Zinc,. Copper, Magnesium, Proteins and Superoxide Dismutase in Leprosy Patients on Multidrug Therapy—a Follow-Up Study," *Indian J. Lepr.*, Oct.-Dec. 1996, vol. 68, No. 4, pp. 325-333.

Shaheen, A. A. et al., "Effect of Various Stressors on the Level of Lipid Peroxide Antioxidants and $Na^+, K+^+$-ATPase Activity in Rat Brain," Experientia, 1996, vol. 52, pp. 336-339.

Singer, G. M. et al., "Mutagenicity and Chemistry of *N*-Nitroso-*N*-(*p*-substituted-benzyl)methylamines," Journal of Medicinal Chemistry, Mar. 1983, vol. 26, No. 3, pp. 309-312, 1st page only.

Supinski, G. et al., "Effect of Free Radical. Scavengers on Diaphragmatic Fatigue," *Am. J. Respir. Cri. Care Med.*, Feb. 1997, vol. 155, No. 2, pp. 622-629.

Szabo, M. E, et al, "Direct Measurement of Free Radicals in Ischemic/Reperfused Diabetic Rat Retina," *Clin. Neurosci.*, 1997, vol. 4, No. 5, pp. 240-245.

Tardieu, M. et al., "Derivatized Dextrans Mimic Heparin as Stabilizers, Potentiators, and Protectors of Acidic or Basic FGF," *Journal of Cellular Physiology*, 1992, vol. 150, pp. 194-203.

Wiessler. M. et al., "Biological Activity of Benzylating N-Nitroso Compounds, Models of Activated N-Nitrosomethylberzylamine," *Carcinogenesis*, 1983, vol. 4, No. 7, pp. 867-871.

Graham, M. F. et al., "Isolation and Culture of Human Intestinal Smooth Muscle Cells," *Proceedings of the Society for Experimental Biology and Medicine*, 1984, vol. 176, No. 4, pp. 503-507.

\* cited by examiner

FIG. 2
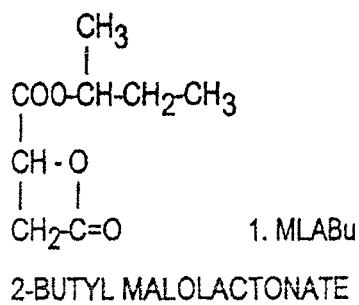
1. MLABu
2-BUTYL MALOLACTONATE
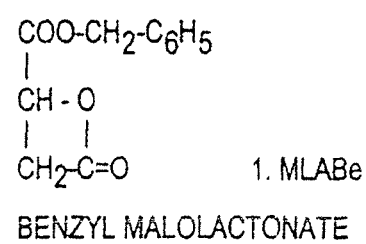
1. MLABe
BENZYL MALOLACTONATE
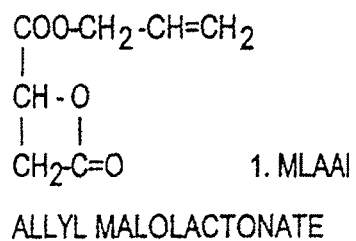
1. MLAAl
ALLYL MALOLACTONATE
STRUCTURE OF THE
3 β-LACTONES

SYNTHESIS OF ALKYL MALOLACTONATE FROM DL-ASPARTIC ACID

R = -CH(CH3) -CH2-CH3, BENZYL MALOLACTONATE OR -CH (CH3) -CH2-CH3
(2-BUTYL MALOLACTONATE) OR -CH2-CH=CH2 (ALLYL MALOLACTONATE)

SYNTHESIS OF DERIVATIVES OF POLY (β - MALIC ACID)

FIG. 6

TABLE PRESENTING FOR EACH OF THE REFERENCED RGTA AND CORRESPONDING TO THE POLYMERS OF TYPE $CM_nDS_m$, THE PERCENTAGES BY DEFINITION OF FREE GROUPS X AND Y. Z = NOTHING

| Reference | | X = % COO- | Y = % SO3- | Z |
|---|---|---|---|---|
| RGTA 1000 | $CM_1D$ | 48.98 | 0 | 0 |
| RGTA 1001 | $CM_1DS_{0.5}$ | 48.5 | 13.1 | 0 |
| RGTA 1002 | $CM_1DS_{0.75}$ | 44.7 | 25.3 | 0 |
| RGTA 1003 | $CM_1DS_1$ | 40.9 | 40.6 | 0 |
| RGTA 1004 | $CM_1DS_{1.5}$ | 31.7 | 56.5 | 0 |
| RGTA 1005 | $CM_1DS_2$ | 26.3 | 82.3 | 0 |
| RGTA 1006 | $CM_1DS_{ex}$ | 19.1 | 94.4 | 0 |
| RGTA 1007 | $CM_2D$ | 91.8 | 0 | 0 |
| RGTA 1008 | $CM_2DS_{0.5}$ | 84.9 | 18.4 | 0 |
| RGTA 1009 | $CM_2DS_{0.75}$ | 63.7 | 30.3 | 0 |
| RGTA 1010 | $CM_2DS_1$ | 61.1 | 37.3 | 0 |
| RGTA 1011 | $CM_2DS_{1.5}$ | 57.8 | 44.6 | 0 |
| RGTA 1012 | $CM_2DS_2$ | 55.0 | 55.7 | 0 |
| RGTA 1013 | $CM_2DS_{ex}$ | 22.6 | 58.5 | 0 |
| RGTA 1014 | $CM_3D$ | 118.3 | 0 | 0 |
| RGTA 1015 | $CM_3DS_{0.5}$ | 102.7 | 15.6 | 0 |
| RGTA 1016 | $CM_3DS_{0.75}$ | 70.9 | 36.5 | 0 |
| RGTA 1017 | $CM_3DS_1$ | 87.3 | 42.0 | 0 |
| RGTA 1018 | $CM_3DS_{1.5}$ | 71.2 | 55.0 | 0 |
| RGTA 1019 | $CM_3DS_2$ | 68.9 | 57.3 | 0 |
| RGTA 1020 | $CM_4D$ | 154.0 | 0 | 0 |
| RGTA 1021 | $CM_4DS_{0.5}$ | 114.8 | 8.9 | 0 |
| RGTA 1022 | $CM_4DS_1$ | 104.9 | 24.6 | 0 |
| RGTA 1023 | $CM_4DS_2$ | 72.2 | 51.8 | 0 |
| RGTA 0040 | DS commercial | 0 | 97.6 | 0 |
| RGTA 1024 | $DS_{0.5}$ equiv | 0 | 103.0 | 0 |
| RGTA 1025 | $DS_{0.25}$ equiv | 0 | 41.4 | 0 |
| RGTA 1026 | $DS_{0.125}$ equiv | 0 | 23.5 | 0 |

FIG. 9
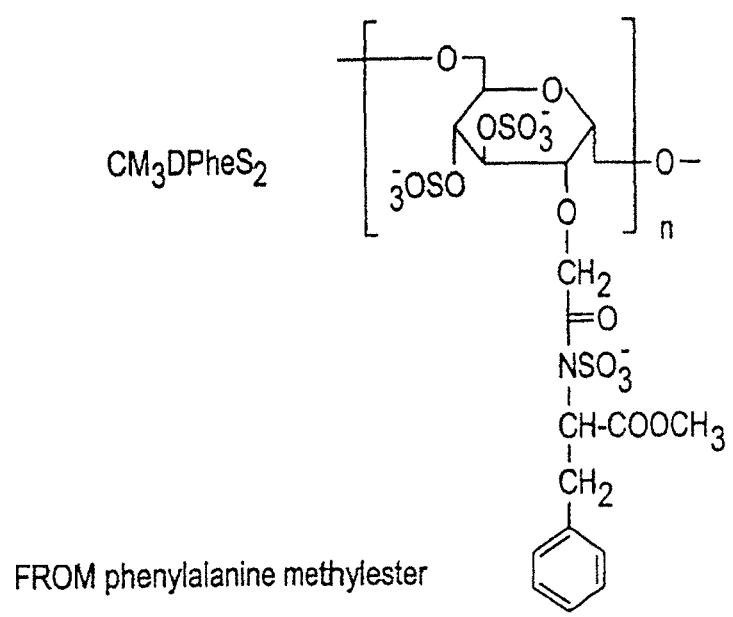
CM3DPheS2
FROM phenylalanine methylester
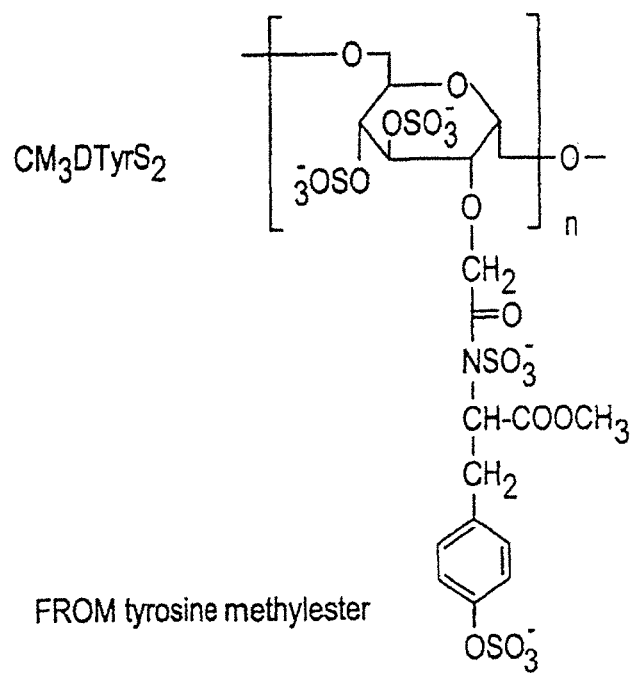
CM3DTyrS2
FROM tyrosine methylester FIG. 10
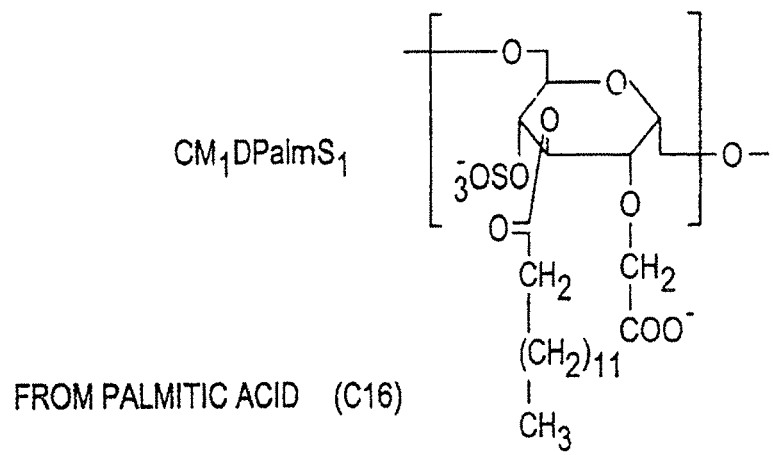
CM₁DPalmS₁
FROM PALMITIC ACID (C16)
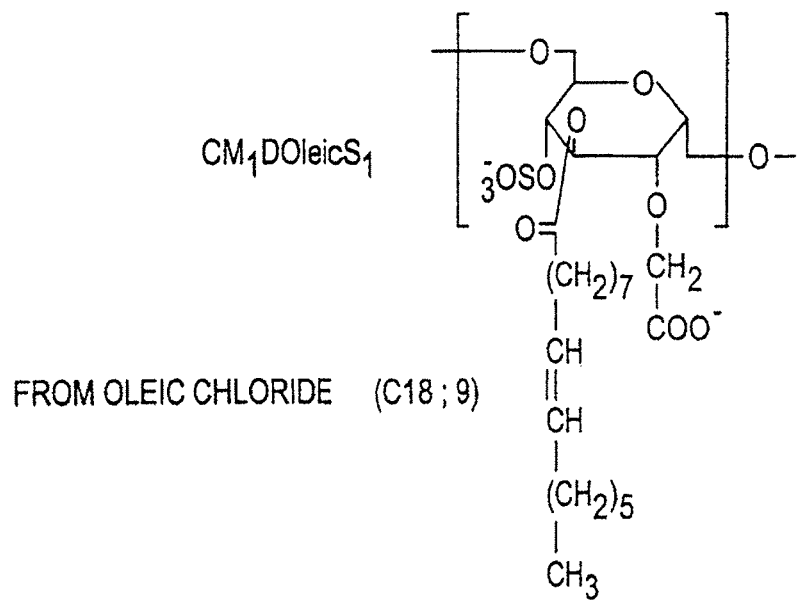
CM₁DOleicS₁
FROM OLEIC CHLORIDE (C18 ; 9)

FIG. 11

ANTICOAGULANT ACTIVITIES OF THE POLYMERS

| Reference | polymers | Activity of anti-coagulant in IU | Reference | polymers | Activity of anti-coagulant in IU |
|---|---|---|---|---|---|
| Hep | Heparin | 176 | RGTA 1013 | $CM_2DSex$ | <50 |
| RGTA 2010 | Pcoo- | <50 | RGTA 1014 | $CM_3D$ | <50 |
| RGTA 2011 | P1S | <50 | RGTA 1015 | $CM_3DS_{0.5}$ | <50 |
| RGTA 2012 | P2S | <50 | RGTA 1016 | $CM_3DS_1$ | <50 |
| RGTA 1000 | $CM_1D$ | <50 | RGTA 1017 | $CM_3DS_{1.5}$ | <50 |
| RGTA 1001 | $CM_1DS_{0.5}$ | <50 | RGTA 1019 | $CM_3DS_2$ | <50 |
| RGTA 1002 | $CM_1DS_{0.75}$ | <50 | RGTA 1110 | $CM_2DPhSS1$ | <50 |
| RGTA 1003 | $CM_1DS_1$ | <50 | RGTA 1111 | $CM_2DES1$ | <50 |
| RGTA 1004 | $CM_1DS_{1.5}$ | <50 | RGTA 1112 | $CM_2DPheS2$ | <50 |
| RGTA 1005 | $CM_1DS_2$ | <50 | RGTA 1113 | $CM_3DTyrS2$ | <50 |
| RGTA 1006 | $CM_1DSex$ | <50 | RGTA 1114 | $CM_1DPalmS1$ | <50 |
| RGTA 1007 | $CM_2D$ | <50 | RGTA 1115 | $CM_1DOleicS1$ | <50 |
| RGTA 1008 | $CM_2DS_{0.5}$ | <50 | RGTA 0040 | DS commercial | <50 |
| RGTA 1009 | $CM_2DS_{0.75}$ | <50 | RGTA 1024 | $DS_{0.5}$ equiv | <50 |
| RGTA 1010 | $CM_2DS_1$ | <50 | RGTA 1025 | $DS_{0.25}$ equiv | <50 |
| RGTA 1011 | $CM_2DS_{1.5}$ | <50 | RGTA 1026 | $DS_{0.125}$ equiv | <50 |
| RGTA 1012 | $CM_2DS_2$ | <50 | RGTA 0001 | Dextran T40 | <50 |

FIG. 12

STABILIZING EFFECTS OF THE POLYMERS ON FGF1

| TREATMENT<br>VALUE  ED50 | 20°C<br>0 DAYS | 20°C<br>1 DAY | 20°C<br>7 DAYS | 20°C<br>15 DAYS | 37°C<br>1 DAY | 37°C<br>7 DAYS |
|---|---|---|---|---|---|---|
| FGF1 ALONE | 6 | 8 | 14 | >20 | 7 | >20 |
| FGF1 + Heparin | 0.8 | 1.2 | 6 | 16 | 1.4 | 15 |
| FGF1 + Dextran T40 | 6 | 10 | >20 | >20 | 7 | >20 |
| FGF1 + DS commercial | 6 | 8 | >20 | >20 | 7 | >20 |
| FGF1 + DS$_{0.5}$ equiv | 6 | 8 | >20 | >20 | 7 | >20 |
| FGF1 + DS$_{0.125}$ equiv | 6 | 10 | >20 | >20 | 7 | >20 |
| Pcoo- | 8 | >20 | >20 | >20 | 18 | >20 |
| P1S | 3 | 6 | 10 | 17 | 5 | 15 |
| P2S | 1 | 3 | 9 | 14 | 3 | 11 |
| FGF1 + CM$_1$D | 6 | 9 | >20 | >20 | 7 | >20 |
| FGF1 + CM$_2$D | 6 | 7 | >20 | >20 | 7 | >20 |
| FGF1 + CM$_1$DS2 | 0.5 | 1.1 | 6 | 17 | 2.1 | 16 |
| FGF1 + CM$_2$DS2 | 2 | 8 | 15 | >20 | 5 | >20 |
| FGF1 + CM$_2$DPhS | 8 | 15 | >20 | >20 | 8 | >20 |
| FGF1 + CM$_2$DPhSS1 | 2 | 6 | 18 | >20 | 3 | 14 |
| FGF1 + CM$_2$DES1 | 1 | 3 | 8 | 17 | 9 | >20 |
| FGF1 + CM$_2$DPheS2 | 0.9 | 2 | 4 | 13 | 8 | 17 |
| FGF1 + CM$_3$DTyrS2 | 3 | 5 | >20 | >20 | 9 | >20 |
| FGF1 + CM$_1$DPalmS1 | 4 | 4 | 16 | >20 | 14 | >20 |

FIG. 13

POTENTIATION EFFECTS ON FGF1 AND FGF2

| Reference polymers | Conditions | concentrations (μg/ml) | ED50 FGF1 (ng/ml) | ED50 FGF2 (pg/ml) |
|---|---|---|---|---|
| | FGF ALONE | 0 | 8 | 56 |
| | Heparin | 1 | 2 | 35 |
| RGTA 2010 | Pcoo- | 100 | 4 | 56 |
| RGTA 2011 | P1S | 100 | 2.5 | 38 |
| RGTA 2012 | P2S | 100 | 4 | 41 |
| RGTA 0040 | DS commmercial | 100 | 3 | 30 |
| RGTA 1024 | $DS_{0.5}$ equiv | 100 | 4 | 36 |
| RGTA 1026 | $DS_{0.125}$ equiv | 100 | 6 | 48 |
| RGTA 1000 | $CM_1D$ | 10 | 12 | 168 |
| RGTA 1007 | $CM_2D$ | 10 | 16 | 297 |
| RGTA 1005 | $CM_2DS2$ | 10 | 1 | 40 |
| RGTA 1012 | $CM_2DS2$ | 10 | 1.5 | 31 |
| RGTA 1110 | $CM_1DPhS1$ | 10 | 8 | 53 |
| RGTA 1111 | $CM_2DES1$ | 10 | 5 | 45 |
| RGTA 1112 | $CM_2DPheS2$ | 10 | 3 | 38 |
| RGTA 1113 | $CM_3DTyrS2$ | 10 | 2 | 30 |
| RGTA 1114 | $CM_1DPalmS1$ | 10 | 9 | 42 |

FIG. 14

PERCENTAGE OF FGF1, FGF2 AND TGFβ NOT
DEGRADED BY TRYPSIN IN THE PRESENCE
OF THE POLY (β-MALIC ACID) POLYMERS

|  | polymer + FGF2 | | | | polymer + FGF1 | | | | polymer + TGFβ | | | |
|---|---|---|---|---|---|---|---|---|---|---|---|---|
| concentration (μg/ml) | 500 | 50 | 5 | 0.5 | 500 | 50 | 5 | 0.5 | 100 | 50 | 5 | 0.5 |
| FGF2 ALONE | 100 | | | | 100 | | | | 100 | | | |
| FGF2 + trypsin | <1 | | | | <1 | | | | <1 | | | |
| Heparin (10 μg/ml) | 100 | | | | 100 | | | | <1 | | | |
| trypsin + Pcoo- | 14.4 | 24.4 | 18 | 22 | 29.7 | 25 | 18 | 16 | 5 | <1 | <1 | <1 |
| trypsin + P1S | 61.3 | 100 | 97 | 87.5 | 85 | 96 | 100 | 63 | 58 | 84 | 70 | 22 |
| trypsin + P2S | 59 | 68 | 65 | 57 | 72 | 84 | 91 | 49 | 33 | 75 | 92 | 67 |

FIG. 15

PERCENTAGE OF FGF2 & TGFβ NOT DEGRADED
BY TRYPSIN IN THE PRESENCE OF THE POLYMERS
DERIVED FROM DEXTRANS

| Polymers | % protection of the factors | | Polymers | % protection of the factors | |
|---|---|---|---|---|---|
| | FGF2 | TGFβ | | FGF2 | TGFβ |
| Heparin | 100 | 15 | $CM_3D$ | 22 | 23 |
| $CM_1D$ | 20 | 25 | $CM_3DS_{0.5}$ | 29 | 32 |
| $CM_1DS_{0.5}$ | 74 | 65 | $CM_3DS_1$ | 32 | 38 |
| $CM_1DS_{0.75}$ | 77 | 71 | $CM_3DS_{1.5}$ | 35 | 40 |
| $CM_1DS_1$ | 80 | 75 | $CM_3DS_2$ | 40 | 47 |
| $CM_1DS_{1.5}$ | 96 | 78 | $CM_2DPhSS1$ | 76 | 67 |
| $CM_1DS_2$ | 100 | 80 | $CM_2DES1$ | 81 | 71 |
| $CM_1DSex$ | 100 | 81 | $CM_2DPheS2$ | 67 | 56 |
| $CM_2D$ | 20 | 25 | $CM_3DTyrS2$ | 83 | 54 |
| $CM_2DS_{0.5}$ | 87 | 74 | $CM_1DPalmS1$ | 67 | 74 |
| $CM_2DS_{0.75}$ | 90 | 77 | $CM_1DOleicS1$ | 58 | 72 |
| $CM_2DS_1$ | 97 | 80 | DS commercial | 87 | 12 |
| $CM_2DS_{1.5}$ | 95 | 79 | $DS_{0.5}$ equiv | 66 | 9 |
| $CM_2DS_2$ | 90 | 80 | $DS_{0.125}$ equiv | 51 | 10 |
| $CM_2DSex$ | 88 | 74 | Dextran T40 | 6 | 5 |

FIG. 16

INHIBITORY EFFECTS OF THE POLYMERS
ON THE ACTIVITIES OF LEUKOCYTE ELASTASE AND PLASMIN

|  | IC 50 | mg/ml |  | IC 50 | mg/ml |
|---|---|---|---|---|---|
| Polymers | Elastase | plasmin | Polymers | Elastase | plasmin |
| Heparin | 1.8 | 1 | $CM_2DSex$ | 5 | 0.07 |
| Pcoo- | 100 | 53 | $CM_3D$ | >100 | >100 |
| P1S | 2 | 0.98 | $CM_3DS_{0.5}$ | 8 | 6 |
| P2S | 4.7 | 0.82 | $CM_3DS_1$ | 6 | 6 |
| $CM_1D$ | >100 | >100 | $CM_3DS_{1.5}$ | 4 | 6 |
| $CM_1DS_{0.5}$ | 37 | 8 | $CM_3DS_2$ | 2 | 1.5 |
| $CM_1DS_{0.75}$ | 24 | 2.5 | $CM_2DPhS1$ | 12 | 2.4 |
| $CM_1DS_1$ | 20 | 1 | $CM_2DES1$ | 18 | 3.8 |
| $CM_1DS_{1.5}$ | 3 | 0.15 | $CM_2DPheS2$ | 4 | 0.3 |
| $CM_1DS_2$ | 1 | 0.08 | $CM_3DTyrS2$ | 1.8 | 0.15 |
| $CM_1DSex$ | 1 | 0.035 | $CM_1DPalmS1$ | 1.4 | 6 |
| $CM_2D$ | >100 | >100 | $CM_1DOleicS1$ | 2 | 9 |
| $CM_2DS_{0.5}$ | 7 | 1 | DS commercial | >100 | >100 |
| $CM_2DS_{0.75}$ | 5 | 0.7 | $DS_{0.5}$ equiv | >100 | >100 |
| $CM_2DS_1$ | 2 | 0.5 | $DS_{0.25}$ equiv | >100 | >100 |
| $CM_2DS_{1.5}$ | 2 | 0.1 | $DS_{0.125}$ equiv | >100 | >100 |
| $CM_2DS_2$ | 2 | 0.05 | Dextran T40 | >100 | >100 |

FIG. 17
PERCENTAGES OF MUSCULAR REGENERATION AFTER INJECTION OF VARIABLE DOSES OF POLYMERS

| Products | doses µg/ml | Effects in % of the control | Products | doses µg/ml | Effects in % of the control |
|---|---|---|---|---|---|
|  |  | 100 | CM1DS1 | 50 | 134 |
| Dextran T40 | 10 | <100 |  | 100 | 189 |
|  | 50 | <100 |  | 200 | 231 |
|  | 100 | <100 | CM2D | 50 | <100 |
|  | 200 | <100 |  | 100 | <100 |
| Heparin | 10 | <100 | CM2DS2 | 20 | 143 |
|  | 50 | 120 |  | 50 | 138 |
|  | 100 | <100 |  | 100 | 191 |
|  | 200 | <100 |  | 200 | 213 |
| DS commercial | 100 | 112 | CM3D | 50 | <100 |
|  | 200 | 124 |  | 100 | <100 |
| $DS_{0.5}$ equiv | 100 | <100 | CM3DS2 | 50 | 136 |
|  | 200 | 121 |  | 100 | 147 |
| $DS_{0.25}$ equiv | 100 | 109 |  | 200 | 178 |
|  | 200 | 125 | $CM_2DPhS1$ | 50 | 115 |
| $DS_{0.125}$ equiv | 100 | <100 |  | 100 | 178 |
|  | 200 | 129 |  | 200 | 189 |
| Pcoo- | 50 | <100 | $CM_2DES1$ | 50 | 137 |
|  | 100 | <100 |  | 100 | 144 |
|  | 200 | <100 |  | 200 | 168 |
| P1S | 50 | 150 | $CM_2DPheS2$ | 50 | 152 |
|  | 100 | 199 |  | 100 | 196 |
|  | 200 | 135 |  | 200 | 154 |
| P2S | 50 | 152 | $CM_3DTyrS2$ | 50 | 167 |
|  | 100 | 170 |  | 100 | 241 |
|  | 200 | 177 |  | 200 | 203 |
| CM1D | 50 | <100 | $CM_1DPalmS1$ | 50 | 133 |
|  | 100 | <100 |  | 100 | 157 |
|  | 200 | <100 |  | 200 | 176 |

FIG. 18

MODULATION OF THE IN VITRO ACTIVITY OF SOD BY THE POLYMERS: PROTECTIVE & POTENTIATING EFFECTS OF TWO RGTA, RGTA 1005(CM1DS2) AND RGTA 1113 (CM3DTyrS2) ON THE IN VITRO ACTIVITY OF SOD.

| Experimental conditions | Activity of sod in arbitrary units |
|---|---|
| SOD CONTROL at pH = 7 | 100 |
| 50 microg/mL of CM1DS2 + SOD at pH = 7 | 132 |
| 250 microg/mL of CM1DS2 + SOD at pH = 7 | 165 |
| 500 microg/mL of CM1DS2 + SOD at pH = 7 | 196 |
| 50 microg/mL of CM3DTyrS2 + SOD at pH = 7 | 105 |
| 250 microg/mL of CM3DTyrS2 + SOD at pH = 7 | 122 |
| 500 microg/mL of CM3DTyrS2 + SOD at pH = 7 | 118 |
| SOD CONTROL at pH = 3 | 20 |
| 50 microg/mL of CM1DS2 + SOD at pH = 3 | 65 |
| 250 microg/mL of CM1DS2 + SOD at pH = 3 | 115 |
| 500 microg/mL of CM1DS2 + SOD at pH = 3 | 130 |
| 50 microg/mL of CM3DTyrS2 + SOD at pH = 3 | 85 |
| 250 microg/mL of CM3DTyrS2 + SOD at pH = 3 | 133 |
| 500 microg/mL of CM3DTyrS2 + SOD at pH = 3 | 150 |
| SOD CONTROL at pH = 11 | 30 |
| 50 microg/mL of CM1DS2 + SOD at pH = 11 | 40 |
| 250 microg/mL of CM1DS2 + SOD at pH = 11 | 95 |
| 500 microg/mL of CM1DS2 + SOD at pH = 11 | 122 |
| 50 microg/mL of CM3DTyrS2 + SOD at pH = 11 | 65 |
| 250 microg/mL of CM3DTyrS2 + SOD at pH = 11 | 93 |
| 500 microg/mL of CM3DTyrS2 + SOD at pH = 11 | 110 |

FIG. 19

PROTECTIVE EFFECT OF THE POLYMERS ON SOD AFTER TREATMENT BY TRYPSIN AND THERMAL SHOCK

| Polymers 100 mg/ml | % of residual activity SOD + Trypsin | % of residual activity SOD at 60°C | Polymers 100 mg/ml | % of residual activity SOD + Trypsin | % of residual activity SOD at 60°C |
|---|---|---|---|---|---|
| Control | 0 | 0 | $CM_3D$ | 0 | 0 |
| Heparin | 60 | 45 | $CM_3DS_{0.5}$ | 55 | 60 |
| Pcoo- | 0 | 0 | $CM_3DS_1$ | 30 | 40 |
| P1S | 70 | 80 | $CM_3DS_2$ | 10 | 20 |
| P2S | 80 | 80 | $CM_4D$ | 0 | 0 |
| $CM_1D$ | 0 | 0 | $CM_4DS_{0.5}$ | 60 | 100 |
| $CM_1DS_{0.5}$ | 90 | 70 | $CM_4DS_1$ | 80 | 100 |
| $CM_1DS_{0.75}$ | 100 | 70 | $CM_2DPhSS1$ | 50 | 60 |
| $CM_1DS_1$ | 100 | 90 | $CM_2DES1$ | 60 | 80 |
| $CM_1DS_{1.5}$ | 95 | 75 | $CM_2DPheS2$ | 80 | 100 |
| $CM_1DS_2$ | 100 | 85 | $CM_3DTyrS2$ | 80 | 100 |
| $CM_1DSex$ | 90 | 90 | $CM_1DPalmS1$ | 75 | 60 |
| $CM_2D$ | 0 | 0 | $CM_1DOleicS1$ | 70 | 50 |
| $CM_2DS_{0.5}$ | 90 | 55 | DS commercial | 20 | 10 |
| $CM_2DS_1$ | 100 | 70 | $DS_{0.5}$ equiv | 30 | 20 |
| $CM_2DS_{1.5}$ | 70 | 85 | $DS_{0.25}$ equiv | 20 | 0 |
| $CM_2DS_2$ | 90 | 60 | $DS_{0.125}$ equiv | 20 | 0 |
| $CM_2DSex$ | 70 | 40 | Dextran T40 | 0 | 0 |

POTENTIATION EFFECT OF SOD PRODUCED IN VITRO
BY ACTIVATED MONOCYTES

FIG. 21

INHIBITORY EFFECTS OF THE RGTA ON CALPAINE

| Polymers | % of residual activity |
|---|---|
| Dextran T40 | 100 |
| $CM_1D$ | 100 |
| $CM_1DS_{0.5}$ | 30 |
| $CM_1DS_1$ | 10 |
| $CM_1DS_{1.5}$ | 0 |
| $CM_1DS_2$ | 0 |
| $CM_1DSex$ | 20 |
| $CM_2D$ | 100 |
| $CM_2DS_{0.5}$ | 10 |
| $CM_2DS_1$ | 0 |
| $CM_2DS_2$ | 0 |
| $CM_2DSex$ | 10 |
| $CM_2DPhSS1$ | 10 |
| $CM_2DES1$ | 0 |
| $CM_2DPheS2$ | 0 |
| $CM_3DTyrS2$ | 0 |
| $CM_1DPalmS1$ | 35 |
| $CM_1DOleicS1$ | 50 |
| DS commercial | 100 |

FIG. 22

INHIBITORY EFFECTS OF THE RGTA ON HEPARITINASE

| % of residual activity | Heparanase | % of residual activity | Heparanase |
|---|---|---|---|
| Dextran T40 | 0 | $CM_3D$ | 0 |
| $CM_1D$ | 0 | $CM_3DS_{0.5}$ | 90 |
| $CM_1DS_{0.5}$ | 60 | $CM_3DS_1$ | 100 |
| $CM_1DS_1$ | 100 | $CM_3DS_2$ | 100 |
| $CM_1DS_{1.5}$ | 100 | $CM_4D$ | 0 |
| $CM_1DS_2$ | 100 | $CM_4DS_1$ | 75 |
| $CM_1DSex$ | 100 | $CM_4DS_2$ | 60 |
| $CM_2D$ | 0 | $CM_2DPhSS1$ | 80 |
| $CM_2DS_{0.5}$ | 80 | $CM_2DES1$ | 90 |
| $CM_2DS_1$ | 100 | $CM_2DPheS2$ | 100 |
| $CM_2DS_2$ | 100 | $CM_3DTyrS2$ | 100 |
| $CM_2DSex$ | 100 | $CM_1DPalmS1$ | 60 |
| DS commercial | 100 | Heparin | 100 |

ACTIONS OF THE RGTA ON THE SECRETION OF COLLAGENS IN VITRO BY THE HISM CELLS SUBJECTED TO IONIZING RADIATION OF $^{60}$CO

PROTECTIVE EFFECTS OF THE RGTA ON THE SURVIVAL OF CELLS SUBJECTED TO $^{60}Co$ IRRADIATION

FIG. 26

ANTIFIBROTIC ACTION OF THE RGTA ON PIG AORTA SMOOTH MUSCLE CELLS

| | Inhibition of Proliferation | IC50 Inhibition in µgM | (%) Synthesis collagen / proteins | Collagen Type 1 in % of the Total 1+3+5 | Collagen Type 3 in % of the Total 1+3+5 | Collagen Type 5 in % of the Total 1+3+5 |
|---|---|---|---|---|---|---|
| Dextran T40 | 0 | | 17.1 | 58.7 | 36.9 | 4.4 |
| $CM_1D$ | 0 | | 17.6 | 59.1 | 35.8 | 5.1 |
| $CM_1DS_2$ | 85 | 0.62 | 11.4 | 58.1 | 21.8 | 14.1 |
| $CM_2DS_1$ | 75 | 0.47 | 9.3 | 58.7 | 15.8 | 25.5 |
| $CM_2DPheS_2$ | 85 | 1.12 | 12.1 | 68.5 | 18.5 | 13.0 |
| $CM_3DTyrS_2$ | 80 | 0.95 | 10.8 | 65.5 | 20.6 | 13.9 |
| Heparin | 82 | 0.36 | 15.5 | 73.0 | 20.9 | 6.1 |

EFFECTS OF THE RGTA ON THE REGULATION
OF THE OSSEOUS MASS AND ON THE QUALITY OF ITS RESTRUCTURING.
EXAMPLE OF A CHRONIC PERIODONTAL DISEASE

BIOCOMPATIBLE POLYMERS, PROCESS FOR THEIR PREPARATION AND COMPOSITIONS CONTAINING THEM

RELATED APPLICATION

This application is a divisional of U.S. application Ser. No. 13/160,999, filed Jun. 14, 2011, which is a continuation of U.S. application Ser. No. 12/212,093, filed Sep. 17, 2008, which is a continuation of patent application Ser. No. 10/695,574, filed Oct. 28, 2003, which is a divisional of application Ser. No. 09/765,788, filed Jan. 19, 2001 now U.S. Pat. No. 6,689,741, issued Feb. 10, 2004), which is a continuation of International Application No. PCT/FR99/01774, with an international filing date of Jul. 20, 1999, which claims priority to French Patent Application No. 98/09309, filed Jul. 21, 1998, the disclosure of the prior applications are incorporated in its entirety by reference.

TECHNICAL FIELD

This invention pertains to new biocompatible polymers, a process for their preparation and compositions containing them.

BACKGROUND

Known in the prior art are polymer derivatives of dextrans obtained by substitution by carboxymethyl, carboxymethyl-benzylamide and carboxymethyl-benzylamide-sulfonate residues. These polymers, the process for their preparation and their properties, are described in French Patent No. 2,461,724 as well as in U.S. Pat. No. 4,740,594. Among these polymers, certain of them imitate the properties of heparin and can be used as plasma substitution products because of their anticoagulant and anticomplement properties. Others imitate a different property of heparin which consists of a stabilization, protection and potentiation of the in vitro biological activity of the growth factors of the FGF family (Tardieu et al., Journal of Cellular Physiology, 1992, 150, pages 194 to 203). Furthermore, French Patent No. 2,644,066 describes the use of carboxymethyl-benzylamide-sulfonate derivatives of dextran, referred to as CMDBS, alone or associated with FGFs, for cicatrization.

More recently, French Patent Nos. 2,718,023, 2,718,024 and 2,718,026 proposed the use of polymers capable of protecting, stabilizing and potentiating growth factors that have an affinity for heparin, such as the fibroblast growth factors or an FGF and Transforming Growth Factor beta (TGFβ), as a drug for the treatment of lesions of the gastrointestinal tract, nervous system and muscle tissues, respectively. To illustrate this protective effect of the CMBDS dextran derivatives, these patents present the results of the proteolytic digestion by trypsin of $FGF_1$, $FGF_2$ or TGFβ. These properties of protection, stabilization and potentiation of the growth factors with an affinity for heparin enabled characterization of a new class of polymers, designated as HBGFPP to indicate "Heparin-Binding Growth Factor Protector and Potentiator", that exhibit cicatrizing and repair activities in relation to muscle, nervous and gastrointestinal tract tissues, and which are devoid of anticoagulant activity at the doses employed.

In addition to the above HBGFPP applications, French Patent No. 2,718,025 proposes the use of these polymers as drugs for the treatment of inflammations. This anti-inflammatory activity is illustrated by the in vitro inhibitory action against proteolytic enzymes implicated in the inflammatory reaction such as leukocyte elastase or plasmin and in vivo by histological studies demonstrating a reduced inflammatory cellular reaction in tissues treated by CMDBS dextran derivatives.

However, these CMDBS dextran derivatives are compounds which are difficult to synthesize and present the risk of salting out residues that are known for their toxic effects such as benzylamine. Furthermore, the applications of the HBGFPP and thus of the CMDBS proposed in the prior art are limited solely to the repair and cicatrization of certain tissues.

SUMMARY

The invention relates to a biocompatible polymer constituted by a sequence of identical or different components of the general formula (I): $A_aX_xY_y$, in which A represents a monomer, X represents a carboyxl group fixed on a monomer A, Y represents a sulfate or sultanate group fixed on a monomer A; a represents the number of monomers A, x represents the substitution rate of the set of monomers A by the groups X, y represents the substitution rate of the set of monomers A by the groups Y. The invention also relates to the pharmaceutical or diagnostic compositions containing at least one polymer of general formula (I).

BRIEF DESCRIPTION OF THE DRAWINGS

FIG. 2 shows selected structures of three β-lactones.

FIG. 6 is a table representing selected polymers of type $CM_nDS_m$ and the percentages of three groups X, Y and Z.

FIG. 9 shows the structures of $CM_3DPheS_2$ and $CM_3DTyrS_2$.

FIG. 10 shows the structures of $CM_1DPalmS_1$ and $CM_1DOleicS_1$.

FIG. 11 is a table showing anti-coagulant activities of selected polymers.

FIG. 12 is a table showing the stabilizing effects of selected polymers on $FGF_1$ FIG. 13 is a table showing the potentiation effects of $FGF_1$ and $FGF_2$ for selected polymers.

FIG. 14 is a table showing the percentage of $FGF_1$ and $FGF_2$ and TGFβ not degraded by trypsin in the presence of poly(β-malic acid) polymers.

FIG. 15 is a table showing the percentage of $FGF_2$ and TGFβ not degraded by trypsin in the presence of polymers of the invention derived from dextrans.

FIG. 16 is a table showing the inhibitory effects of selected polymers of the invention on the activities of leukocyte elastase and plasmin.

FIG. 17 is a table showing percentages of muscular regeneration after injection of various doses of polymers.

FIG. 18 is a table showing modulation of the in vitro activity of SOD by selected polymers of the invention.

FIG. 19 is a table showing the protective effect of selected polymers of the invention on SOD after treatment by trypsin and thermal shock.

FIG. 21 is a table showing the inhibitory effects of selected polymers of the invention on calpaine.

FIG. 22 is a table showing the inhibitory effects of selected polymers of the invention on heparitinase.

FIG. 26 is a table showing the antifibrotic action of selected polymers of the invention on pig aorta smooth muscle cells.

DETAILED DESCRIPTION

Figure 1:
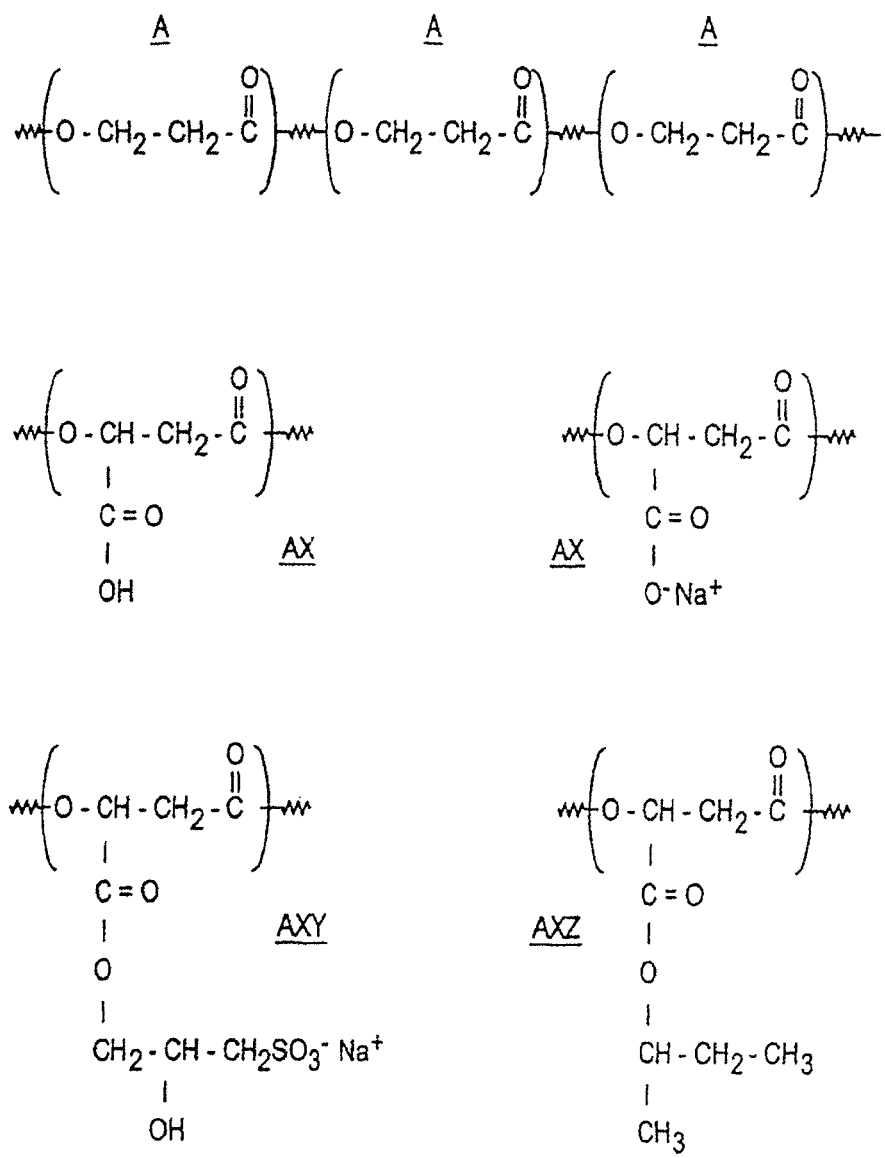
FIG. 1 shows formulas of selected β-malic acids.

This invention resolves the drawbacks of the prior art by providing new biocompatible polymers which are easy to prepare and present the properties of the HBGFPP but also, in an unexpected manner, novel properties which enable very extensive fields of application, especially in therapeutics, which are not limited to just a few types of particular organs, tissues or cells. The polymers of the invention are, therefore, referred to below as "RGTA" for "ReGeneraTing Agents".

The polymers of the invention have a molar mass greater than about 5,000 da and are constituted by a sequence of identical or different components of the following general formula (I):

in which:
A represents a monomer,
X represents a carboxyl group fixed on a monomer A and contained within a group according to the following formula: —R—COO⁻R¹, in which R is a bond or an aliphatic hydrocarbon chain, possibly branched and/or unsaturated, and which can contain one or more aromatic rings, with the exception of benzylamine and benzylamine sulfonate, and R¹ represents a hydrogen atom or a cation,
Y represents a sulfate or sulfonate group fixed on a monomer A and contained within a group according to one of the following formulas: —R—O—SO₃—R¹, —R—SO₃—R¹, in which R is a bond or an aliphatic hydrocarbon chain, possibly branched and/or unsaturated, and which can contain one or more aromatic rings, with the exception of benzylamine and benzylamine sulfonate, and R¹ represents a hydrogen atom or a cation,
a represents the number of monomers A, which is such that the mass of the polymers of formula (I) is greater than approximately 5,000 da,
x represents the substitution rate of the set of monomers A by the groups X, which is comprised between approximately 20 and 150%, preferably on the order of 50%,
y represents the substitution rate of the set of monomers A by the groups Y, which is comprised between approximately 30 and 150%, preferably on the order of 100%.

The radical R of the groups X and Y in formula (I) is advantageously selected from among an alkyl, allyl, aryl, linear or branched group.

In the definition of the substitution rates cited above, a substitution rate x of 100% is understood to mean that each monomer A of the polymer of the invention contains statistically one X group. Similarly, a substitution rate y of 100% is understood to mean that each monomer of the polymer of the invention contains statistically one Y group. Substitution rates higher than 100% manifest the fact that each monomer bears statistically more than one group of the type under consideration. Conversely, substitution rates lower than 100% manifest the fact that each monomer bears statistically less than one group of the type under consideration.

The polymers offer the remarkable advantage of presenting in vivo a slow degradability, which differentiates them from the heparan sulfates which are products that are naturally and rapidly degraded by heparinase or heparitinase. Furthermore, the polymers of the invention neither contain nor release toxic products after degradation, in contrast to the CMDBS, which have benzylamine groups.

The monomers A which constitute the base elements of the polymers of formula I can be identical or different, and are selected from among all types of monomers such as, for example, those proposed for the HBGFPP such as the sugars, esters, alcohols, amino acids, nucleotides and the like. Among these, preference is given especially to the -oses, and especially to glucose.

The number of monomers A is defined in a manner such that the mass of the polymers of the invention is greater than approximately 5,000 da. Consequently, the RGTA can be constituted by diverse homomeric as well as heteromeric polymerizable structures such as, for example: the polyester copolymers of biosynthesis or chemical synthesis such as the aliphatic polyesters or those of natural origin such as the polyhydroxylalcanoates. Also applicable are polysaccharides and their derivatives of bacterial origin such as cellulose, xanthan, dextran and the like, unicellular or multicellular plant extracts such as starch, plant cellulose or alginates or their derivatives, the fucanes and their derivatives and the like, or animal extracts such as hyaluronic acid or chitin and the like, or products of synthesis such as those obtained by copolymerization. Synthesized proteins such as the natural or chemically modified polyamino acids such as, for example, collagen can also be employed in the constitution of the polymers of the invention.

The selection of the polymer structure of the RGTA is based on the various forms of presentation which can be used depending on the tissue or the organ to be treated or the physicochemical characteristics such as the solubility, the spatial conformation with the solutions, suspensions, gels, powders, sponges, films, compact moldable materials, porous, semiporous or nonporous materials, materials that crumble or materials that do not crumble, materials that erode and materials that do not erode, materials that can be colonized or materials that can not be colonized, etc.

Heparin or its fragments with weak anticoagulant properties and natural heparan sulfates and their fragments are excluded from the scope of the present invention because:
Their anticoagulant activity can be greater than 50 IU. In fact, the polymers of the invention are devoid of significant anticoagulant activity, i.e., they present an activity lower than about 50 IU/milligram compared to that of heparin whose activity is on the order of 150 to 170 IU/milligram.

They exhibit biodegradability under the action of enzymes of the heparinase or heparitinase type which is too rapid to enable the biological effects obtained in the context of this invention.

The polymers of the invention can also comprise functional chemical groups, designated Z, which are different from X and Y, and capable of conferring on the polymers of the invention supplementary biological or physicochemical properties. Thus, the groups Z are useful for conferring on the RGTA a better solubility or lipophilic properties enabling better diffusion or tissue penetration, for example, increasing the amphiphilic properties, enabling crossing the blood-brain barrier and the like. As an example, the groups Z, which can be identical or different, can be amino acids, fatty acids, fatty alcohols, ceramides or derivatives thereof, or nucleotide addressing sequences.

The groups Z can also represent identical or different active agents, such as therapeutic or diagnostic agents, for example, an anti-inflammatory, antimicrobial, antibiotic and the like or an enzyme, a growth factor and the like.

The polymers of the invention in which Z is present have the following formula II:

$$A_a X_x Y_y Z_z$$

in which A, X, Y, a, x, and y have the same meanings as defined above and z represents the substitution rate of the set of monomers A by the groups Z, which is comprised between approximately 0 and 50%, preferably on the order of 30%. The groups X, Y and Z can be fixed directly on the monomer A or fixed to each other with only one of them being fixed to the monomer A. Thus, the groups Z can be fixed by covalence directly on the monomers A or fixed by covalence on the groups X and/or Y.

However, the groups Z can also be conjugated to the polymers of formula (I) by bonds other than covalent bonds, such as ionic or hydrophilic interactions, depending on the nature of A, X and Y. The polymers of the invention can then constitute a vectorization system of Z. Thus, the polymers of the invention are useful for transporting an active agent Z, such as a growth factor or an enzyme, to the level of the injured or diseased tissue as defined below in the context of the applications of the polymers of the invention.

The polymers in which the groups R of X and Y or the groups Z are capable of inducing toxic effects directly or after degradation are not included within the scope of this invention. Among the groups Z excluded from the invention can be cited those groups constituting mutagenic agents or those known to be carcinogenic or exhibiting other toxic properties. This is the case of benzylamine which can be precipitated out from the benzylamide group contained in the CMDBS and the carcinogenic properties of which are well known by the expert in the field (Wiessler M, et al., Carcinogenesis 1983; 4(7): 867-871; Singer G M, et al., J. Med. Chem. 1983; 26(3): 309-312). CMDBS is consequently excluded from the polymers of the invention.

The invention also pertains to the pharmaceutical or diagnostic compositions containing at least one polymer as defined above associated in the composition with a pharmaceutically acceptable vehicle. These compositions can be used in humans as well as in animals. In fact, as with the HBGFPP described in the prior art, the polymers of the invention present the following properties:

They are devoid of significant anticoagulant activity, which means that they present an activity lower than about 50 IU/milligram compared to that of heparin the activity of which is on the order of 150 to 170 IU/milligram.

They stabilize and potentiate the growth factors that exhibit an affinity for heparin and particularly, as an example, $FGF_1$ and/or $FGF_2$ and $TGF\beta$.

They protect these factors against proteolytic agents such as trypsin.

They inhibit the protease activities implicated in the inflammatory process such as, for example, leukocyte elastase or plasmin.

They exert a cicatrizing effect in at least the models presented in the cited patents 613 muscles, nerves or the gastrointestinal tract.

Thus, the polymers of the invention constitute a new class of agents that promote the repair of muscle and nervous tissues, and those of the gastrointestinal tract and which present, as reported in U.S. Pat. No. 5,693,625 for the CMDBS, properties on cutaneous cicatrization and that of the cornea or on flat bone as described by Blanquaert F et al. (Bone, 1995; 17(6): 499-506). However, the polymers of the invention also present unexpected properties in relation to the CMDBS. As an example, we can cite the effect of the CMDBS on cranial bone defects (Blanquaert F et al., Bone, 1995; 17(6): 499-506) which a priori is not transposable to long bone. Flat bone and long bone are of a completely different nature because:

They are of different embryological origin. Flat bone is a derivative of the conjunctive tissue cells whereas long bone is a derivative of the cartilaginous cells.

Flat bone is a spongy bone and does not contain a medullary cavity in contrast to long bone.

Flat bone does not cicatrize naturally when there is a loss of substance such as upon trepanation as can be seen by the absence of cicatrization in the crania originating from prehistoric civilizations such as the Incas or Egyptians (see for example Evidence for stone age cranial surgery, 7000 BC, Nature, 1997, 367, 360). Surprisingly, the polymers of the invention present effects on the repair of very severe bone defects on the order of a third of the length of the diaphysis of a rat femur. Not only was repair observed with reformation of an osseous shaft but also the shaft was filled with marrow, i.e., the treatment with RGTA led to the reformation of a true medullary cavity whereas in the absence of RGTA the defect is simply packed with disorganized osseous material. The same is true of cutaneous incisions because this repair is of such high quality that there is practically no trace of a scar.

The invention, therefore, pertains more particularly to the previously described biocompatible polymers of formulas (I) and (II) which are devoid of significant anticoagulant activity. These polymers present an anticoagulant activity lower than about 10 IU/mg at single or daily doses comprised:

between about 0.001 mg and about 1 mg per cm3 when the application is local, between about 0.1 mg/kg and about 100 mg/kg when the administration is via the systemic route, for example, via the intravenous route, between about 0.2 mg/kg and about 500 mg/kg when the administration is via the intramuscular route, between about 0.1 mg/kg to about 5 g/kg when administered orally.

The anticoagulant activity of the polymers of the invention at the doses indicated above is for a person weighing about 70-kg lower than:

about 10 IU for a local application,
about 100 IU for an intravenous administration,
about 500 IU for an intramuscular administration.

Remarkably, the polymers of the invention are devoid of significant anticoagulant activity at the doses specified above but still present the capacity of preserving or restoring tissue homeostasis. The invention, therefore, pertains particularly to the use of the aforementioned polymers for the preparation of a drug that is useful for the prevention or treatment of dysfunctions of tissue homeostasis and which do not present significant anticoagulant activity.

In a completely surprising manner, we found that the polymers of the invention can be administered via routes other than those described in the prior art for the CMDBS which only envisaged local administration at the level of the injured tissue. Thus, it is possible to select among the polymers of the invention those which are suitable, for example, because of their solubility, for the selected route of administration: intravenous, intra-arterial, intramuscular, intraperitoneal, intraocular, into the cerebrospinal fluid or directly into the central nervous system to cross over the blood brain barrier, as well as orally. All of these routes of administration, possibly even combined, have been shown to be particularly effective.

Thus, the invention concerns pharmaceutical compositions in which the polymer of the invention is associated with a pharmaceutical vehicle in a form enabling oral, cutaneous, subcutaneous, topical, intramuscular, intravenous or intra-arterial administration or administration into any of the fluid compartments of the organism. Studies performed in the framework of this invention revealed that the RGTA act especially within the dosage windows beyond which satisfactory biological effects were not always obtained. These optimal effective doses are defined below and depend on the route of administration and the type of lesion.

Advantageously, in a manner to completely cover the surface of a wound or to fill the volume of a tissue lesion, the pharmaceutical compositions are dosed to allow administration of about 0.001 to about 1 milligram of polymer per square centimeter or of about 0.005 to about 1 milligram of polymer per cubic centimeter of tissue to be treated. Thus, the compositions of the invention preferably contain between about 0.01 and about 10 milligrams of polymer per milliliter of physiological solution of dissolution.

For administration via the systemic route (venous, arterial), via the intraperitoneal route or intraocular route, into the cerebrospinal fluid, into the intracochlear fluid or into any peritissular or intratissular fluids, the compositions of the invention are dosed to allow administration of between about 0.1 and about 100 milligrams of polymer per kilogram of weight of the human or animal to be treated.

For administration via the intramuscular route, the compositions of the invention are dosed to allow administration of between about 0.2 and about 500 milligrams of polymer per kilogram of weight of the human or animal to be treated, preferably between about 1 and about 50 mg per kg.

For oral administration, the compositions of the invention are dosed to allow administration of between about 1 and about 5000 milligrams of polymer per kilogram of weight of the human or animal to be treated, preferably between about 10 and about 500 mg per kg.

Furthermore, the previously reported properties of the HBGFPP, i.e., that they present a cicatrizing and repairing activity on the muscle and nervous tissues and on those of the gastrointestinal tract and that they can be used as drugs for the treatment of inflammations, we have demonstrated the remarkable effects of the polymers of the invention on the regulation of the homeostasis of the mass and the functionality of the tissues and organs, demonstrating that they act on tissular and cellular regeneration, protection, preservation and aging in vivo and ex vivo, as well as antifibrotic activities and protective activities against the deleterious effects of ischemias, ionizing radiation and oxidizing products induced by diseases or stress or stemming from food. Consequently, the RGTA should be considered to be regulators of tissular homeostasis in that they regulate the mass of the regenerated tissues and they act on the reorganization of the matrix in that they exert an antifibrotic and cicatricial effect on the tissues and organs subjected to acute as well as chronic destructive processes.

These properties of the RGTA are characterized by unique effects on the quality and rate of the tissue repairs. These effects are manifested by an almost complete reconstitution and identity with the original tissue structure (prior to the lesion) and by the almost complete absence of cicatricial traces such as in particular signs of fibrosis or loss of its functional integrity. More particularly, the research results which will be presented below in the experimental part demonstrated the in vivo tissue protection and regeneration properties of the RGTA in the following models:

cutaneous wound lesion,
regeneration of osseous tissues such as long bones with the example of the femur,
protection against the loss of osseous tissue and regulation of its restoration in a model of chronic periodontal disease,
protection against the deleterious effects of ionizing radiation,
protection against the deleterious effects of ischemias irrespective of their location.

Thus, the properties below of the polymers of the invention have been particularly demonstrated:

A protective effect against the deleterious effects linked to oxidative stress and to oxidizing agents. The polymers of the invention act in particular as protective agents and potentiators of enzymes such as superoxide dismutase or SOD. This property makes it possible to use the polymers of the invention for the preparation of a drug intended for the treatment and/or the prevention of lesions and disorders induced by oxidative stress and oxidizing agents. But this property also makes it possible to use the polymers of the invention alone or in association with another compound as a preservative for foods or nutriments that naturally contain antioxidants or to which antioxidants, such as animal or plant SOD, were added.

A preservative and .protective effect against ischemias. This property makes it possible to use the polymers of the invention for the preparation of a drug intended for the treatment and/or the prevention of pathologies associated with hypoxia, with cellular degeneration such as the neuropathies, myopathies, hepatopathies, nephropathies, the cardiopathies and the like and to the peroxidations of molecules such as the lipids. This property also makes it possible to use the polymers of the invention in compositions for the preservation of the functionality of tissues and organs especially for the purpose of their conservation, the transport of ex vivo organs, organ transplants, their grafting as well as prostheses.

An inhibitory activity against the enzymes of the calpaine family. This property makes it possible to use the polymers of the invention for the preparation of a drug intended for the treatment and/or prevention of heart diseases and diseases of the nervous system.

An inhibitory activity against the degradation enzymes of heparin or the heparan sulfates such as heparinase or heparitinase. This property makes it possible to use the polymers of the invention for the preparation of a drug intended for the treatment and/or the prevention of the diseases associated with an anarchic growth of the cells and the pathological processes in relation with an angiogenesis.

An action of protecting cells against the effects of ionizing radiation and of both the quantitative and qualitative regulation of the constituents of the cell matrix such as, for example, the collagens, making it possible to increase the survival and functioning of the cells. This activity makes it possible to use the polymers of the invention for the preparation of a drug intended for the treatment and/or prevention of the deleterious effects of ionizing radiation as well as the use of these polymers in the preparation of cosmetic products.

An antifibrotic activity which is manifested in vitro and in vivo by regulatory effects on the proliferation of mesenchymal cells such as the smooth muscle cells, fibroblasts or hepatic cells and the quality of the type of collagen that they secrete, as well as an activity on the phenotypic quality of the collagens synthesized by these cells and by the notable reduction in the fibrotic cicatricial sequelae. This activity makes it possible to use the polymers of the invention for the preparation of a drug intended for the treatment and/or prevention of pulmonary, renal, hepatic, cardiac, vascular and dermatological pathologies as well as pathologies of grafts and their functional integration, of multiple derivatives linked to parasitism.

Thus, unexpectedly, the inventors discovered that the RGTA presented the capacity to:

protect, stabilize the enzymatic activities of superoxide dismutase or SOD, potentiate the enzymatic activities of superoxide dismutase or SOD.

Thus, this enzyme can be protected either in situ and in vivo or ex vivo. The RGTA can, therefore, be used alone as protective agents of endogenous SOD and in this role protect SOD in all of its functions or it can be used in association with SOD in the indications known by those of ordinary skill in the therapeutic and cosmetic fields. Due to this property, the RGTA also act as preservatives of foods or nutrients or nutriments.

The RGTA act as protective and reparative agents of the deleterious effects associated with tissue stress. Thus, in ischemia, regardless of its origin or in response to a cellular or tissular aggression, for example, under the effect of ionizing radiation, or in response to an invasion by a pathogenic agent, regardless of whether it be viral, microbial, parasitic or even of the type causing pathologies of the TSSE (Transmissible Subacute Spongiform Encephalopathies) type such as prions, or during vascular rupture caused by hemorrhages whose effects are harmful by causing functional losses, for example, in the case of hemorrhages of the retinal vessels which can lead to blindness or in the brain which can lead to loss of motor functions or others.

Consequently, the invention pertains to pharmaceutical compositions 'containing at least one RGTA in both human and animal fields of applications. These compositions are beneficial in medical, veterinary and cosmetic fields as well as in alimentary fields as preservatives of foods or nutriments that naturally contain antioxidants or to which are added antioxidants such as animal or plant SOD.

The protective qualities of endogenous SOD or SOD that is provided exogenously are reinforced by the RGTA. Thus, the RGTA can be administered in all cases in which the beneficial effects of SOD have been described.

For the treatment of diseases in which exogenously supplied SOD has been shown to be effective, the therapeutic effects resulting from the protective effect of endogenous SOD can then act more effectively in the presence of RGTA. The RGTA limit or avoid exogenous intakes from acting indirectly as antioxidant agents. The following therapeutic effects result from these effects:

Protection against the aggressions of disease or degeneration of the nervous tissues. For example in stress (Shahen et al., Effects of various stressors on the level of lipid peroxide antioxidants and $Na^+$, $K^+$-ATPase activity in brain, Experentia, 1996, 52, 336-339) or of neuronal degeneration and the neurodegenerative diseases associated with vascular accidents, traumatic accidents or of pathologies such as Parkinsonism in which the protective activity of endogenous SO.D enables a more intensive effect (Bostantjopoulos et al., Superoxide dismutase activity in early and advanced Parkinson's disease, Funct. Neurol., 1997, 12, 63-68).

Aging due to an antiapoptosis effect (Fernandez Novoa et al., Methods Find Exper Clin Pharmacol, 1997, 9, 99-106).

An antioxidant protection in ischemias of the limbs. The RGTA can be administered by itself in this application. The protective provided by treatment with SOD alone will be reinforced by the administration of RGTA. In view of the properties described, that the RGTA is beneficial when administered alone and/or in association with SOD in the numerous applications describing the effects of SOD (D'Agnillo and Chang, *Reduction of hydroxyl radical generation in a rat hind limb model of ischemia—reperfusion injury using cross-linked hemoglobin—superoxide dismutase—catalase*, Artif. Cells Blood Substiti Immobil Biotechnol, 1997, 25, 163-80).

The administration of RGTA alone or in association with SOD would be beneficial against disorders of the heart, brain and central nervous system as in the case of lesions of the spinal cord (Nakauchi et al., *Effects of lecithinized superoxide dismutase on rat spinal cord injury*, J. Neurotrauma, 1996, 13, 573-82) or of the retina.

In the treatment of respiratory insufficiencies associated with 'diaphragmatic fatigue (Supinski et al., *Effects of free radical scavengers on diaphragmatic fatigue*, Am. J. Respir. Crit. Care Med., 1997, 155, 622). This could be notably of value in patients with muscular dystrophy.

All tissues, especially those for which the endogenous active SOD level is higher (vascular endothelial cells, in the liver, the kidneys, the cardiac and skeletal muscles, the pancreas, the epithelial cells of the intestinal mucosa, the colon, the trachea, the esophagus, the conjunctive tissue and cartilage).

The treatment of the deleterious effects associated with diabetes such as the diabetic retinopathies (Szabo et al., *Direct measurement of free radicals in ischemic/reperfused diabetic rat retina*, Clin. Neurosci., 1997, 4, 240-5).

The treatment of leprosy (*Serum, zinc, copper, magnesium, proteins and superoxide dismutase in leprosy patients on multidrug therapy—a follow-up study*, Indian J. Lepr., 1996, 68, 325-53).

In the treatment of endotoxic shock (*Hepatic response to the oxidative stress induced by E. coli endotoxin*, Mol. Cell. Biochem. 1996, 159, 115-121).

In the treatment of the lesions induced by the stress caused by the presence of pathogenic agents of all types, especially viruses, including the AIDS virus, or the agents that induce TSSE such as the prions.

In the preventive and/or curative treatment against irradiations. Thus, the adverse effects of radiotherapy can be reduced by a preventive and/or curative treatment with RGTA. The use of the RGTA allows reduction of the dose of radiotherapy under cancer treatment conditions (*Prevention of radioinduced cystisi by orgotein, a randomized study*, Anticancer Res., 1996, 16, 2025-8) or enable prevention of the clastogenic effects induced by the irradiation. The hyperthermic effects associated with radiotherapy can be diminished by the use of RGTA in the same manner as SOD (Kandasamy et al., *Involvement of superoxide dismutase and glutathione peroxidase in attenuation of radiation-induced hyperthermia by interleukin 1 alpha in rats*, Brain Res., 1993, 606, 106-10).

In the protection against the effects induced by Ultraviolet radiation, for example on the retina. (Oguni et al., *Chronic retinal effects by ultraviolet irradiation with special reference to superoxide dismutase*, Histol. Histopathol., 1996, 11, 695-702) and the treatment of uveitis (Koch et al., *Effects of different antioxidants on lens-induced uveitis*, Ger. J. Ophthalmol., 1996, 5; 1185-8). The treatment with RGTA can be alone or in association with SOD and its use can be medical as well as cosmetic.

In the treatment of hypertension. In fact, the activity of endogenous SOD is diminished in subjects with hypertension (Jun Ke Yan and Catalano, *Increased superoxide anion production in humans, a possible mechanism for the pathogenesis of hypertension*, J. Hum. Hypertens. 1996, 10, 305-309). The intake of RGTA can have the effect of augmenting this activity and reducing the hypertension.

In the treatment of inflammatory diseases such as arthritis.

The RGTA are also useful for the conservation of organs or tissues as well as in the maintenance of biological fluids such that the following applications can be envisaged:

In the biological fluids such as blood and its cellular constituents, for example, in hemodialysis.

For the preservation of organs in the case of grafts or ex vivo treatment or in reperfusion (Razak et al., *Crosslinked hemoglobin-superoxide dismutase-catalase scavenges free radicals in a rat model of intestinal ischemia-reperfusion injury*, Artif. Cells Blood Substiti Immobil. Biotechnol. 1997, 25, 181-192). The addition of RGTA to solutions for organ conservation and those administered in reperfusion enables preservation of these organs.

The invention pertains to pharmaceutical compositions containing at least one polymer as defined above and intended for the treatment and/or prevention of tissular lesions and disorders, such as those found in traumatology, requiring reparative or plastic surgery of cutaneous or deeper floors such as those of muscles, bone, brain, heart, viscera, etc., in the degenerative diseases possibly associated with fibrosis, in the losses of tissue mass such as osteoporosis or myopathies, in the cardiovascular and neurological fields, in dermatology, etc.

A remarkable property of the RGTA is their capacity to fix themselves on the injured tissues, which enables the use of the RGTA as targeting vectors in a therapeutic and/or diagnostic objective. Consequently, the polymers of the invention can be coupled to molecules, represented above by the group Z, endowed with therapeutic activities or to molecules that facilitate the repair of the injured tissue.

Other advantages and characteristics of the invention will become manifest from the examples below concerning, on the one hand, the preparation of polymers of the invention in which the polymer skeleton is of the polyester type or of a polysaccharide nature and, on the other hand, the properties of the polymers of the invention.

A) Preparation of the Polymers of the Invention

EXAMPLE 1

Synthesis of Poly (β-malic acid) Derivatives from a Non-Polysaccharide Skeleton

In this example, the polymer of the invention is a copolymer of β-malic acids of general formula (II), the components A of which, substituted by X and/or Y and/or Z, are represented in FIG. 1. In FIG. 1:

A is —(O—$CH_2$—$CH_2$—CO)—
X is —COON or —$COO^-Na^+$
Y is —CO—$CH_2$—CHOH—$CH_2$—$SO_3H$ or —CO—$CH_2$—CHOH—$CH_2$—$SO^{3-}Na^+$
Z is —CO—$OCH_3$—CH($CH_2$—$CH_3$)—$CH_3$
x, y and z correspond to the percentages of the X, Y and Z groups shown in Table I below in relation to the different polymers synthesized.

TABLE I

| Reference | Type of polymer | Carboxylic groups = X | Sulfonate groups = Y | Hydrophobic groups = Z |
|---|---|---|---|---|
| RGTA 2010 | Pcoo⁻ | 100% | 0% | 0% |
| RGTA 2011 | P1S | 60% | 10% | 10% |
| RGTA 2012 | P2S | 75% | 11% | 12% |

Pcoo⁻ corresponds to a polymer composed exclusively of carboxylic or carboxylate groups X. P1S and P2S correspond to polymers composed of sulfonate groups Y and hydrophobic butyl groups Z in addition to the groups X.

The synthesis of this polymer proceeds from the preparation of β-substituted β-lactones and is followed by an anionic polymerization by ring opening. The three β-lactones synthesized are shown in FIG. 2.

Figure 3:
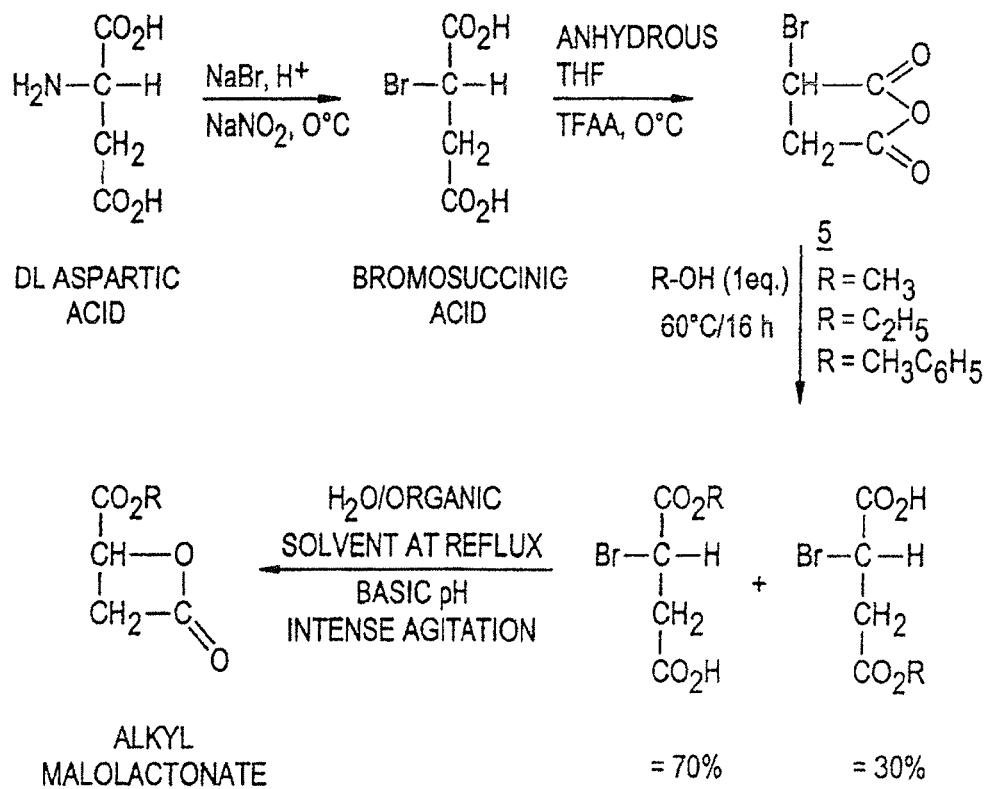
FIG. 3 shows the synthesis of alkyl malolactonate from DL-aspartic acid.

The monomers are obtained from DL-aspartic acid in four steps prior to the polymerization as shown in FIG. 3.

The synthesis of the alkyl malolactonate is performed from DL-aspartic acid in which R represents —$CH_2$—$C_6H_5$ (benzyl malolactonate) or —CH($CH_3$)—$CH_2$—$CH_3$ (2-butyl malolactonate) or $CH_2$—CH=$CH_2$ (allyl malolactonate).

I—Synthesis of the Monomers (Aspartic Acid Pathway)

1) Synthesis of (2R,S) bromosuccinic acid

Synthesis of (2R,S) bromosuccinic acid is obtained after a diazotation reaction of DL-aspartic acid. For this reaction, the carbon bearing the amine group undergoes a double inversion of configuration (Guerin et al., Optically active poly(β-malic acid), 1985, Polymer Bulletin, 14: 187).

100 g (0.75 moles) of DL-aspartic acid and 415 g (4.04 moles; 5.5 eq.) of sodium bromide are dissolved in 1620 milliliters of 2N sulfuric acid in an ice bath. Then 62 g (0.9 moles; 1.2 eq.) of sodium nitrite are added in small quantities, under agitation. Thirty minutes after the end of this addition, the rectional medium is neutralized with 8 g (0.13 moles; 0.18 eq.) of urea for 30 minutes at room temperature. The bromosuccinic acid is extracted with 1 liter of ethyl acetate and the aqueous phase washed with 1 liter of ethyl acetate. The organic phases are dried over magnesium sulfate, filtered on a Büchner funnel then the ethyl acetate is eliminated in the Rotavapor.

The bromosuccinic acid is then recrystallized 4 times in acetonitrile, filtered on a Büchner funnel then dried for 4 h at 45° C. under vacuum in a desiccator.

Characteristics: MW=197; m=52.8 g; Yield of 36%; mp=168° C.; appearance: white powder.

2) Synthesis of the Monoesters

The synthesis of the monoesters comprises the prior preparation of the anhydride without racemization of the chiral centers. The anhydride is synthesized from (2R,S) 2-bromosuccinic acid under the action of a dehydrating agent, trifluoroacetic anhydride (TFAA), under anhydrous conditions and under nitrogen. The following step is the opening of the anhydride by an alcohol which leads to two monoesters, only one of which will be lactonizable. The choice of the alcohol is based on the nature of the desired lactone.

a) Synthesis of Benzyl Bromosuccinate

Fifty g (0.25 moles) of bromosuccinic acid are degassed under a nitrogen stream for 2 h. In an ice bath, 125 milliliters of anhydrous tetrahydrofuran (THF) then 43.4 milliliters (0.30 moles; 1.2 eq.) of trifluoroacetic anhydride (TFAA) are added drop by drop by a dropping funnel. The solution is left for 2 h at room temperature under agitation, then the THF, the TEA formed and the TFAA in excess are eliminated in the Rotavapor. The bromosuccinic anhydride is allowed to degas for 2 hours.

Then 27.7 milliliters (0.25 moles; 1 eq.) of benzyl alcohol are added. The solution is agitated at 40° C. under an inert atmosphere for 12 h. The mixture of monoesters obtained in this mariner is dissolved in 150 milliliters of ether. The etherized phase is washed 3 times with 100 milliliters of water, dried on magnesium sulfate and filtered on a Büchner funnel.

Characteristics: MW=287; in =71.3 g; Yield of 95%; appearance: pale yellow oil.

b) Synthesis of Allyl Bromosuccinate

The same protocol as previously employed is used but 17.86 milliliters (0.25 moles; 1 eq.) of allyl alcohol are added. The rectional medium is agitated for 22 h at 60° C. under an inert atmosphere rather than for 12 h at 40° C. The monoesters are purified in identical manner.

Characteristics: MW=237; in =17.6 g; Yield of 72.8%; appearance: viscous oil.

c) Synthesis of 2-butyl bromosuccinate

The same protocol as above in 2)b), but with 18.8 g (1 eq.) of $(RS)_2$-butanol that has been distilled in advance. The rectional medium is agitated for 12 hours at 60° C. under an inert atmosphere.

Characteristics: MW=253; m=45 g; Yield of 90%; appearance: orangish yellow oil.

3) Synthesis of the Lactones

The lactonization reaction is performed on the sole lactonizable monoester and presents an inversion of configuration. It is performed directly on the mixture of monoesters after neutralization at pH 7.2 with 2N soda. The reaction takes place in a dichloromethane/water biphasic medium. The lactone is purified by silica column chromatography. The nature of the eluent varies depending on the nature of the lactone. This lactone is then distilled on an appropriate column.

a) Synthesis of Benzyl Malolactonate 71 g (of which 70% is lactonizable monoester, i.e., 0.173 moles) of the mixture of monoesters are dissolved in 300 milliliters of ether and 250 milliliters of water in a balloon flask. A 2N solution of sodium hydroxide is added drop by drop until reaching pH 7.2, then 450 milliliters of dichloromethane are added. The flask is placed on a refrigerant system and the biphasic system is strongly agitated for 3 h at 40° C.

After decantation, the organic phase is washed 2 times with 250 milliliters of water then 2 times with 250 milliliters of brine, dried over magnesium sulfate and filtered. The solvent is eliminated in the Rotavapor. This lactone is purified on silica column (eluent: 8/2 dichloromethane/petroleum ether) and distilled 3 times under vacuum.

Characteristics: MW=206; m=20.7 g prior to purification, i.e. a yield of 40.5%; m=3.41 g after purification, i.e., a yield of 6.7%; by=116-118° C. under $3 \cdot 10^{-2}$ mbar; IR (m, cm$^{-1}$); $''$(CO lactone)=1825 cm$^{-1}$; $''$(CO ester) =1740 cm$^{-1}$; appearance: colorless oil.

b) Synthesis of Allyl Malolactonate

According to the same protocol as above in 3)a), but the pH of the aqueous phase is 7.8 rather than 7.2 and the solution is agitated for 5 h rather than 3 h. The lactone is purified on silica column (eluent: 4/6 petroleum ether/ethyl ether) and is distilled 3 times under vacuum.

Characteristics: MW=156; m=15.3 g prior to purification, i.e., a yield of 53.4%; m=4 g after purification, i.e., a yield of 13%; by=62-65° C. under $3 \cdot 10^{-2}$ mbar; IR (m, cm$^{-1}$): $''$(CO lactone)=1825 cm$^-$; $''$(CO ester)=1740 cm$^{-1}$; appearance: colorless liquid.

c) Synthesis of 2-butyl malolactonate

The same protocol is employed as in 3)a) above. The lactone is purified on silica column (eluent: 8/2 dichloromethane/petroleum ether) and is distilled 3 times under vacuum.

Characteristics: MW=172; m=26.7 g prior to purification, i.e., a yield of 55%; m=14.4 g after purification, i.e., a yield of 28%; by=80-82° C. under $3 \cdot 10^{-2}$ mbar; IR (m, cm$^{-1}$): $''$(CO lactone)=1825 cm$^{-1}$; $''$(CO ester)=1740 cm$^{-1}$; appearance: colorless viscous oil.

II—Synthesis of the Polymers

The lactones were polymerized in the presence of tetramethyl ammonium benzoate ($10^{-3}$ eq.) at 37° C. for 15 days. The polymerization was monitored by infrared analysis with observation of the disappearance of the lactone band at 1850 cm$^{-1}$.

1) Synthesis of allyl butyl-co-malate benzyl-co-malate polymalate

Five g (24.2 mmoles) of benzyl malolactonate, 1.4 g (9.3 mmoles) of ally] malolactonate and 0.7 g (4.1 mmoles) of butyl malolactonate are degassed for 2 h and transferred via cannula into a balloon flask containing 471 milliliters of a primer solution (tetraethylammonium benzoate: $10^{-3}$ eq.; $37.72 \cdot 10^{-6}$) at $80 \cdot 10^{-3}$ M which was degassed in advance for 2 h under a nitrogen stream. The copolymerization was performed at 37° C. for 15 days under an inert atmosphere and under agitation. The polymer was then dissolved in a minimum of chloroform. The chains were terminated by addition of a drop of concentrated hydrochloric acid and the polymer was precipitated with ethanol then dried under vacuum at 40° C. for 48 h.

Characteristics; m=4.37 g; yield of 61.5%; Tv=–5° C.; IR (m, cm$^{-1}$): $''$(CO)==1748 cm$^{-1}$; SEC (THF, polystyrene standard); Mn=6600; MW=9200; Ip=1.4; MSEC=10, 000; S 134 (CH=); 168 (C=O lateral chain); 170 (C=O principal chain); appearance: transparent vitreous polymer.

2) Epoxidation of allyl butyl-co-malate benzyl-co-malate polymalate 1.12 g (7.91 mmoles of unsaturated units) of polymer are dissolved in 3 milliliters of anhydrous dichloromethane in a balloon flask. A solution containing 466.34 milligrams (4.69 mmoles; 6 eq.) of metachloroperbenzoic acid (MCPBA) in 2 milliliters of dichloromethane is added by cannula. The mixture is agitated for 24 hours at room temperature. The polymer is then precipitated with ethanol and dried in a desiccator under vacuum.

Characteristics: m=4 g; precipitation yield of 92%; epoxidation reaction yield of 100%.

The molar mass did not change upon epoxidation because MCPBA does not induce a modification of the chain length.

3) Hydrogenolysis of allyl butyl-co-malate benzyl-co-malate polymalate

Four g of the polymer are dissolved in 5 milliliters of freshly distilled dioxane on sodium in a balloon flask. 800 milligrams (20% by weight) of palladium on active charcoal are added and the hydrogenolysis is begun. When the volume of hydrogen consumed no longer increases (24 h after the beginning of the reaction), the hydrogenolysis is stopped. The solution is filtered on Celite and the dioxane is eliminated in the Rotavapor.

Characteristics: m=2 g; hydrogenolysis yield of 100%.

4) Sulfonation of allyl butyl-co-malate benzyl-co-malate polymalate

Four g of polymer (i.e., $5.64 \cdot 10^{-3}$ moles of epoxide) are dissolved in 20 milliliters of water. 2.14 g of sodium bisulfate (2 eq., $11.28 \cdot 10^{-3}$ moles) are added. The pH of the solution is adjusted to 7.4 (Housse-Ferrari, "Preparation and characterization of porous silicas modified by polymers and copolymers of N,N$^1$-dimethyl acrylamide", Thesis, University of Paris VI, Jan. 30, 1990). The solution is left under agitation for 7 h in ice then ultrafiltered for 24 h at 4° C. against water and lyophilized.

Figure 4:
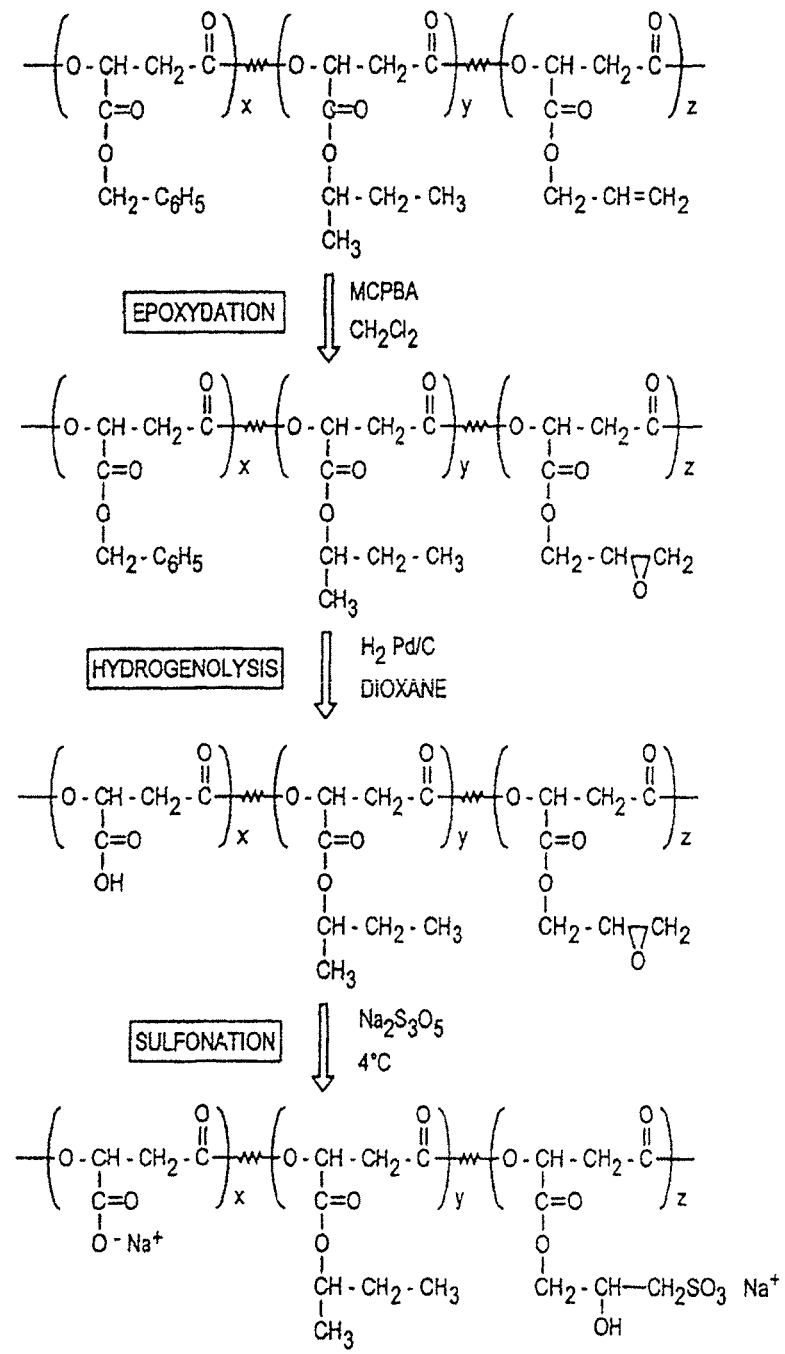
FIG. 4 shows the synthesis of derivatives of poly (β-malic acid).

FIG. 4 summarizes the synthesis steps of the poly(β-malic acid) derivatives.

EXAMPLE 2

Synthesis of Polysaccharide Polymers Constituted by Substituted Glucose Motifs

I—Synthesis of Carboxymethyl Dextran Sulfates Designated CMDS

Figure 5:
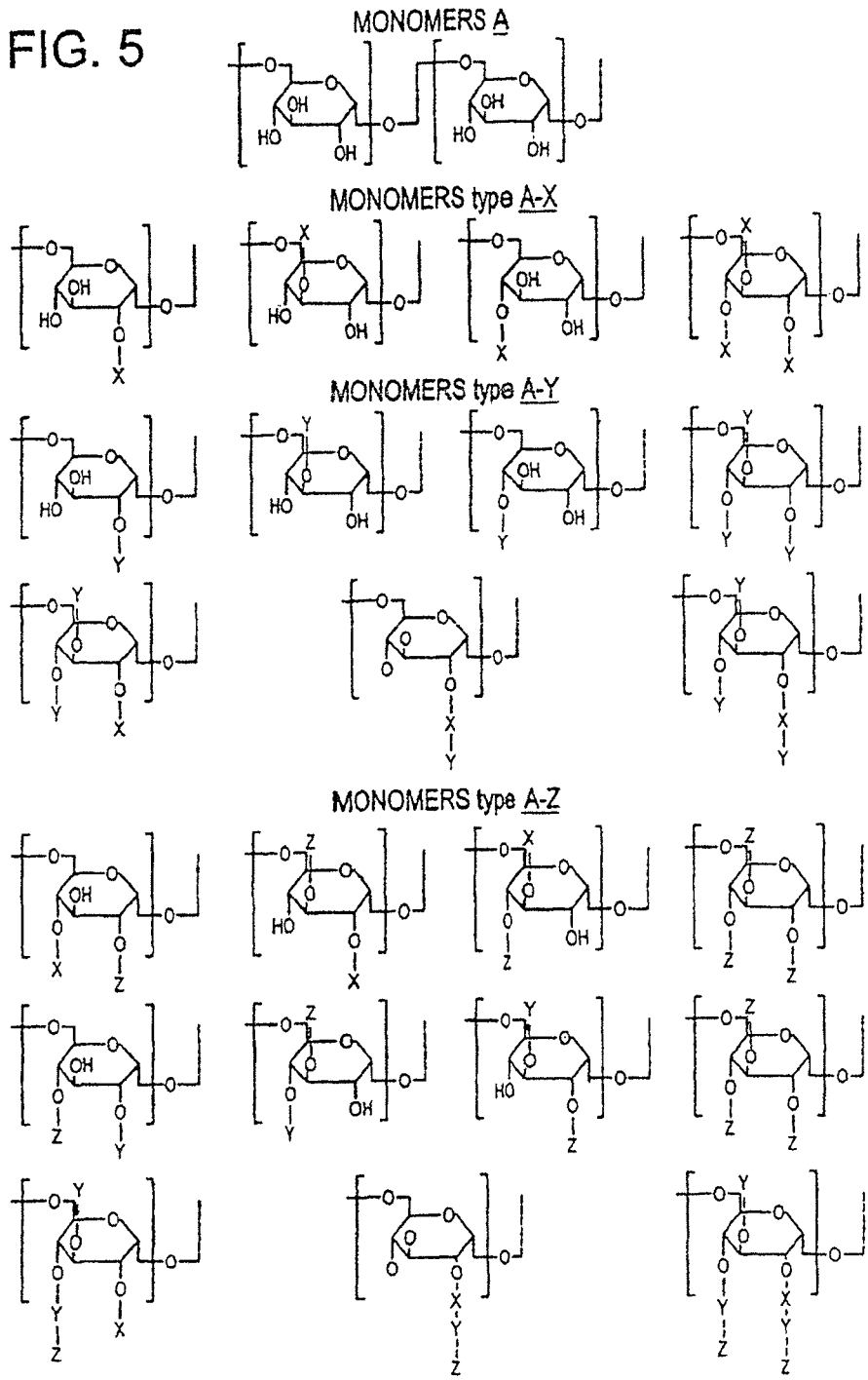
FIG. 5 shows structures of selected monomers A and monomers type A-X, A-Y and A-Z.

In this example, the polymer of the invention is constituted of substituted dextran in which the glucose A motifs substituted by X and/or Y and in which Z is nothing are represented in FIG. 5. The different types of grafting are shown in FIG. 5 in which:

A is a glucose monomer on which X, Y and Z are grafted by the intermediary of the hydroxyl functions in position 2 and/or position 3 and/or position 4 and/or by the intermediary of the Y groups for Z, X is —CH$_2$COOH or —CH$_2$COO$^-$Na$^+$ Y is —SO$_3$H or SO$_3$Na$^+$ Z is a variable group of which several examples are presented below.

The polymers of type CMDS in which Z=nothing contain multiple types of monomers. The first types of substituted monomers are the carboxymethyl glucose of type A-X substituted in position 2 and/or 3 and/or 4 (motifs presented in FIG. 5). The addition of the group Y=(motifs A-Y represented in FIG. 5) corresponds to an O-sulfation and becomes, with R=nothing and R$^1$=H$^+$ or Na$^+$, Y=—O—SO$_3$—H$^+$/Na$^+$. If Y is fixed on X, R of Y becomes CH$_2$—CO and the lost functionality of X (COO$^-$) is no longer considered to exist. It then becomes part of Y and enters into the measurement of the percentages of substitution of the active groups Y.

The different monomers constituting the CMDS polymer are thus either unsubstituted glucose or glucose carboxymethyl or glucose sulfate or glucose carboxymethyl sulfate. The different isomeric forms are diagramed in FIG. 5. Thus the polymers correspond to all of the possible combinations of the different monomeric forms and are defined by the residual rate of free X and Y groups.

The monomers obtained in this manner are either glucose sulfate in position 2, 3 and/or 4 and/or glucose carboxymethyl sulfate. The sulfate is fixed either on the glucose or on the carboxylic group.

Thus, in FIG. 5, in which the bonds of the groups schematized by a dotted line represent the monomers in which all of the circular combinations can be envisaged.

1) Synthesis of Carboxymethyl Dextran Sulfate Designated CM$_n$DS$_m$ a) Carboxymethylation The first dextran carboxymethylation step is performed according to the protocol described in Mauzac et al. (Mauzac et al., Anticoagulant activities of dextran derivatives. Part I: Synthesis and characterization, 1984, Biomaterials 6/61-63). It comprises an etherification of the hydroxyl functions of the glucose residue of the dextran in order to obtain a carboxymethyl dextran. This reaction can be reproduced multiple times and results in products referred to as CM$_n$D in which n represents the number of carboxymethylation steps. The various products referred to as CM$_n$D are characterized by an increasing percentage of COOH. This process thus makes it possible to obtain different rates of carboxymethylation of the dextran as indicated in the table of FIG. 6.

Thus, in a refrigerated 250-milliliter balloon flask, Dextran T40 (37.37 g, 9.34 10$^{-4}$ mole), from Sigma and of molecular weight 40,000 D, is solubilized (182 milliliters of distilled water) at 4° C. A soda solution (74 g, 1.85 mole in 124 milliliters of distilled water), also cooled to 4° C., is poured slowly into the Dextran solution while maintaining constant the temperature of 4° C. Monochloroacetic acid (75.2 g, 0.806 mole), reduced to a fine powder, is added slowly while maintaining the same reaction temperature. However, the temperature of the rectional medium rises at the end of the reaction from 4° C. to 21° C. within several minutes. The mixture is then brought to 50° C. in a thermostated oil bath for 40 minutes. During heating, the rectional medium acquires a yellow coloration. After cooling, the pH is neutralized to 7.2 with glacial acetic acid (Takakura, 1990). The carboxymethyl dextran is collected by precipitation in cold absolute ethanol (5 to 6 times the rectional volume). It is then dried in an oven under vacuum. The polymer CM$_1$D is purified by ultrafiltration then lyophilized (mass=55 g gross).

The presence of the carboxylic ions is quantified by reverse acid-basic quantification using nitric acid. The base used is 1 N soda. The result is expressed in % of COOH groups. % COOH of CM$_1$D=48.98%. This percentage means that statistically approximately one out of every two glucose units was carboxymethylated.

In practice, this reaction can be performed multiple times to attain the desired substitution rates. The same protocol was, therefore, applied for the synthesis of CM$_2$D from CM$_1$D and of CM$_3$D from CM$_2$D:

% COOH of CM$_2$D=91.8% and % COOH of CM$_3$D=118.3%.

b) Sulfatation

The sulfatation reaction of the residual hydroxyl functions after the carboxymethylation steps is performed with chlorosulfonic acid. It produces the compounds referred to as CM$_n$DS$_m$ which are presented in FIG. 6, in which m corresponds to the chlorosulfonic acid equivalents as defined in the example below.

Example of Sulfatation of $CM_1D$

Five hundred milligrams (MW=7.8 mmol/g) of carboxymethyl1dextran ($CM_1D$) are dispersed in 40 milliliters of dry dichloromethane. The number of hydroxyl residues that remain free and capable of reacting in a sulfatation reaction is nOH=$4.10^{-3}$ mole. The reaction was performed in the presence of one chlorosulfonic acid equivalent (nClSO$_3$H=$4.10^{-3}$ mole) or approximately=0.5 g or a volume of 0.3 milliliters, the density of the chlorosulfonic acid solution being 1.75. The 0.3 milliliters of chlorosulfonic acid are diluted in 4 milliliters of dehydrated dichloromethane. The $CM_1DS_1$ obtained in this manner is recovered by filtration of the rectional medium under vacuum on frit.

The same reaction can be performed in the presence of 0.5 or 1.5 or 2 or 3 equivalents of acid chlorosulfonic acid or an excess so as to graft the increasing quantities of O-sulfate groups. The RGTA polymers thereby obtained are referred to as $CM_nDS_m$, with n=1, 2, etc. and m=0.5, 1, 2, etc.

Using the same principle and with the goal of comparing these polymers with other sulfated molecules, we considered as comparison products with the $CM_nDS_m$, either commercial dextran sulfates (Pharmacia Biotech product, code 17-0270-01) or dextrans sulfated from dextran $T_{40}$ in the presence of m equivalents of chlorosulfonic acid, i.e., under reaction conditions comparable to those employed for producing the $CM_nDS_m$.

The results of different quantitative determination of the X groups by titration and the Y groups by elemental analysis of the levels of sulfur atoms make it possible to specify the corresponding values x and y for each of the $CM_nDS_m$ compounds synthesized. These data are presented in FIG. 6. This figure also indicates this percentage for commercial dextran sulfate and for the dextrans sulfated under the same conditions as the $CM_nDS_m$.

Figure 7:
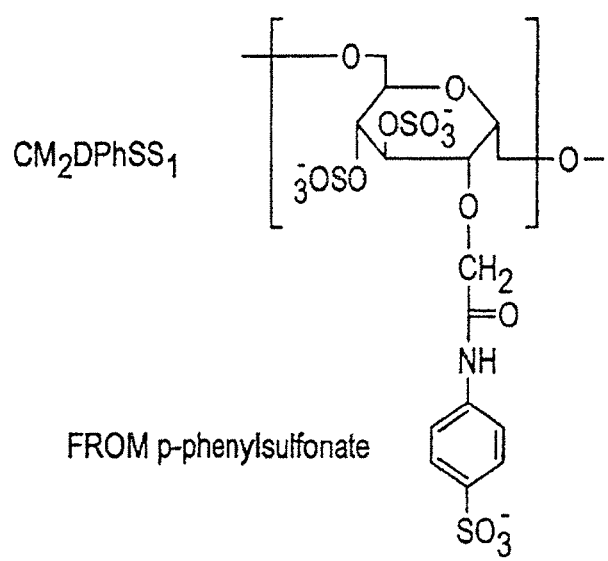
FIG. 7 shows the structure of $CM_2DPhSS_1$.

2) Synthesis of the Carboxymethyl Dextran-Phenyl Sulfonate Polymers Indicated as $CM_2DPhS$ and of a Carboxymethyl Dextran Sulfate Phenyl Sulfonate Designated $CM_2DPhSS$ These polymers are constituted by a sequence of motifs shown in FIG. 7 and correspond to those of FIG. 4 in which Z was nothing. These polymers are constituted by a sequence of motifs of type A-X, A-Y and A-Z as shown in FIG. 6.

In this example, the group Z is phenyl sulfonate indicated as PhS. FIG. 7 shows a monomer A-Z in the case in which Z received as an addition product a carboxyl radical grafted in position 2 of the original glucose, which was itself sulfated in positions 3 and 4.

The polymer $CM_2D$ (2 g; 3.90 mmol) is dissolved in 13 milliliters of distilled water. The pH of the solution is adjusted to 3.5 with 3 M HCl. The coupling agent EEDQ (1.93 g, 2 eq.) is dissolved in 16 milliliters of ethanol (0.12 g of EEDQ/milliliter) at 40° C. The EEDQ solution is added progressively to the polymer and the rectional mixture is strongly agitated for 30 minutes. The phenylsulfanilic acid salt (NH$_2$PhSO$_3$Na, 3-045 g, 2 eq.) is then added in small amounts. The pH of the reaction is adjusted to 9 with soda. The mixture is agitated at room temperature for 4 hours and then neutralized with dilute HCl. The product $CM_2DPhS$ is then ultrafiltered, evaporated under vacuum and then lyophilized (1.66 g).

The elemental and acid-base analyses of the $CM_2DPhS$ yielded: % C=33.9; % H=5.28; % N=0.3; % S=0.67; % COOH=81%.

The elemental and acid-base titrimetric analyses of the polymer $CM_2DPhSS*_1$ yielded % C=23.16; % H=3.72; % N=0.27; % S=9-60; % COOH=52%.

3) Synthesis of a carboxymethyl dextran N and O sulfate derivative

Figure 8:
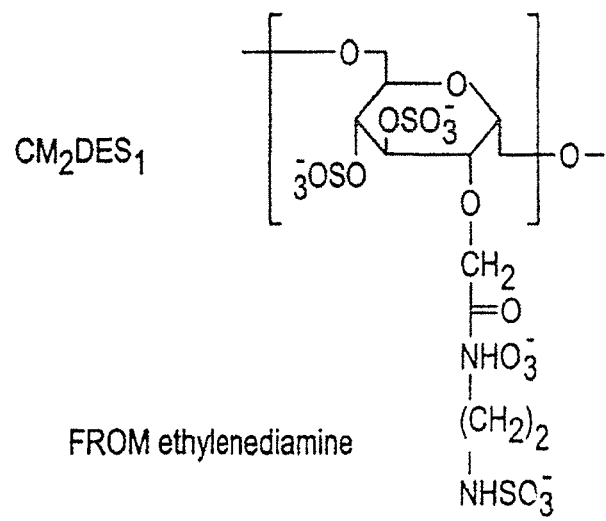
FIG. 8 shows the structure of $CM_2DES_1$.

These polymers are constituted by a sequence of motifs of type A-X, A-Y and A-Z as shown in FIG. 6, in which one of the characteristic motifs A-Z is presented in FIG. 8. In this example, the group Z which is ethylenediamine, indicated as DE, is grafted on the carboxyl radical of the carbon 2 of the original glucose monomer, which is itself sulfated in positions 3 and 4.

The same protocol as employed above was applied to $CM_2D$ with, in a first stage, the addition of an ethylenediamine group Z, indicated as DE, so as to yield the product designated $CM_2DE$.

The elemental and acid-base titrimetric analyses of the polymer $CM_2DE$ showed: % C=37.67; % H=6-25; % N=5.35; % COOH=19%.

The sulfatation protocol was performed on a fraction of this polymer using 1 chlorosulfonic acid equivalent. The products obtained correspond to the $CM_2DES_1$ represented in FIG. 7. In this case, according to the general formula of the RGTA, Z is diethylamine.

The elemental and acid-base titrimetric analyses of the polymer $CM_2DDES_1$ showed: % C=36-83; % H=5.82; % N=4.67; % S=1.82; % COOH=10.7%.

These syntheses make it possible to graft the N-sulfate groups in addition to the O-sulfate groups of the CMDS. These different polymers enable evaluation of the specific roles of the N-sulfate and O-sulfate groups of the $CM_2DES$ in relation to the phenyl sulfonate groups, indicated as PhS, of the compounds $CM_2DPhS$, the sulfate and sulfonate compounds of the $CM_2DPhSS$ or to the compounds. In this type of polymer, it would seem that the sulfate groups are essentially linked to the properties of the RGTA.

4) Synthesis of the polymers of carboxymethyl dextran-phenylalanine sulfate designated $CM_3DPheS$ and of carboxymethyl dextran-tyrosine sulfate designated $CM_3DTrS$ represented in FIG. 9

These polymers are constituted of a sequence of motifs of type A-X, A-Y and A-Z as shown in FIG. 6 in which these characteristic motifs are represented in FIG. 9. In this example, the groups Z are respectively either phenylalanine for Phe or tyrosine for Tyr. They were subjected to the addition process on a carboxyl radical grafted on position 2 of the original glucose which is itself sulfated on positions 3 and 4.

In these polymers, Z is an amino acid with either phenylalanine (Phe) or tyrosine (Tyr) and Y is an —OSO$_3^-$ group.

These syntheses were performed so as to evaluate the importance of the aromatic structures of these two amino acids Phe and Tyr by replacing the benzylamine indicated as B as is known in the CMBDS of the prior art, but the salting out of which in in vivo applications can be detrimental by generating risks of tumorigenicity.

The polymer $CM_3D$ (% COOH=136%, 0.6 g, 3.014 mmol) is dissolved in 6 milliliters of distilled water. The pH of the solution is adjusted to 3.5 with 3M HCl. The coupling agent EEDQ (745 milligrams, 1 eq.) is dissolved in 6.2 milliliters of ethanol at 40° C. The EEDQ solution is added to the polymer drop by drop and the rectional mixture is agitated vigorously for 30 minutes at room temperature. The phenylalanine methyl ester (1.3 g, 2 eq.) is added very slowly to the mixture and the pH is brought from 5 to 9 with soda. The reaction is maintained at room temperature for 4 hours. The solution is then neutralized with dilute HCl. The polymer $CM_3DPhe$ is then ultrafiltered, evaporated under vacuum and then lyophilized (524 milligrams).

The elemental and acid-base titrimetric analyses of the polymer $CM_3DPh$ showed: % C=36.9; % H=5.03; % N=0.44; % COOH=101.05%.

The same protocol was performed on the $CM_3D$ with the tyrosine methyl ester $CM_3DTyr$.

The elemental and acid-base titrimetric analyses of the polymer $CM_3DTyr$ showed: % C=34.41; % H=5.12; % N=0.28; % COOH=101.76%.

The sulfatation protocol was performed on these two polymers using 2 chlorosulfonic acid equivalents.

The elemental and acid-base titrimetric analyses of the polymer $CM_3DPheS*2$ showed: % C=18.08; % H=2.89; % N=0.30; % S=14.71; % COOH=28.79.

The elemental and acid-base titrimetric analyses of the polymer $CM_3DTyrS_2$ showed: % C=17.99; % H=3.13; % N=0.3; % S=14.35; % COOH=19.85.

5) Synthesis of the Lipidic Polymers: Example with Carboxymethyl Dextran-Oleic Acid Sulfate ($CM_1DoleicS$) and Carboxymethyl Dextran-Palmitic Acid Sulfate ($CM_1DpalmS$) Represented in FIG. 10

The polymers are constituted by a sequence of motifs of type A-X, A-Y and A-Z as represented in FIG. 6 in which the characteristic motifs are represented in FIG. 10. In this example, the groups Z, which are respectively either oleic acid indicated as oleic or palmitic acid indicated as palm, were added on the hydroxyl of the carbon 3 of a carboxymethyl glucose in position 2 sulfated in position 4.

These compounds respond to formula (I) in which $Y=$ —$OSO_3^-$ and Z is oleic or palmitic acid. These fatty acids were grafted to evaluate the importance of the hydrophobicity/hydrophilia balance of the polymers in addition to the role itself of these fatty acids.

To the polymer $CM_1D$ (1 g, 2.43 mmol) dissolved in DMSO (16 milliliters) was added triethylamine (0.8 milliliters) and then oleic chloride (1.6 milliliters) was added drop by drop. The rectional mixture was agitated at room temperature for 2 hours. The polymer was precipitated in 120 milliliters of ethyl acetate, centrifuged and then dried under vacuum. The precipitate was dissolved in 20 milliliters of 2M sodium acetate and the salt formed was precipitated in ethanol (160 milliliters), filtered, dissolved in 20 milliliters of distilled water then finally dialyzed against water. After dialysis (24 h), the solution evaporated under vacuum yielded the lipid dextran $CM_1Doleic$ (751 milligrams).

Elemental analysis of the product $CM_1Doleic$: % C=34.25 and % H=5.91.

The same protocol was performed with the palmitic chloride polymer $CM_1Dpalm$.

The elemental analyses of the polymer $CM_1Dpalm$ showed: % C=35.13, % H=5.96.

The sulfatation protocol was performed on these two polymers using 1 chlorosulfonic acid equivalent.

The elemental analyses of the polymer $CM_1DoleicS*1$ showed: % C=28.28; % H=5.04; % S=5.26.

Elemental analyses of the product $CM_1DpalmS*1$ showed: % C=29.17; % H=4.88; % S=5.14.

The different examples presented which involve grafting a group Z yield the compounds, the definitions of several of which are presented in Table II below.

TABLE II

| Reference | Groups | X | Y | Z |
|---|---|---|---|---|
| RGTA 1110 | $CM_2DPhSS_1$ | 52.1 | 43.8 | 8.9 |
| RGTA 1111 | $CM_2DES_1$ | 10.7 | 42.4 | 21.2 |
| RGTA 1112 | $CM_2DPheS_2$ | 28.9 | 56.2 | 17.9 |
| RGTA 1113 | $CM_3DTyrS_2$ | 19.8 | 65.9 | 23.9 |
| RGTA 1114 | $CM_1DpalmS_1$ | 39.8 | 47.4 | 3.8 |
| RGTA 1115 | $CM_1Doleic_1$ | 36.0 | 43.9 | 2.2 |

Table TT above indicates the percentages of substitution of the polymers containing a group Z.

6) Purification Steps for the Different Dextran Derivatives of the Above Examples a) Dialysis to Equilibrium After each synthesis step the polymers are collected in solid form (precipitation or filtration followed by lyophilization). The polymers are then resolubilized in the minimum volume of distilled water and then introduced into dialysis tubing (Spectrapor) with a cut-off threshold of 6000 to 8000 g/mole$^{-1}$. The dialysis is performed against twice-distilled water (MilliQ) in a ratio of 1 volume of product per 50 volumes of water for 4 to 5 days with two changes of water per day.

b) Chromatography

The preceding step is associated with HPLC chromatography on molecular sieve (Column TSK) in order to establish the molar masses of the purified polymers.

c) Tangential Ultrafiltration

After the dialysis, the content of the tubing is ultrafiltered in an ultrafiltration cell (Pellikon, Millipore) on a cellulose membrane with a cut2uuuSthreshold of 10,000 g/mole$^{-1}$. The quality of the purification was monitored with a conductimetry cell. When the conductivity of the water eliminated at the outlet of the cell had returned to the conductivity of pure distilled water (2 μS), the purification was stopped and the solution was concentrated prior to lyphilization.

7) Determination of the Percentages of Substitution

For the two groups of examples presented above, the percentages of substitution of the groups X, Y and possibly Z were determined in the following manner.

a) Poly β-malic acid polymers (Examples 1)

For these polymers, the percentages of substitution are defined a priori in relation to the proportion of the different monoesters subjected to polymerization.

a) Dextran polymers (Examples 2)

Two cases must be envisaged for these polymers obtained from dextran depending on the definition of the group Z.

The first case corresponds to the case of the $CM_nDS_m$ in which Z=nothing; the second case depends on the chemical nature of Z.

On each glucose residue, three hydroxyl functions are capable of reacting. A relative molar mass of 54 g/mole$^{-1}$ is attributed to each hydroxyl function, i.e., one third of the molecular mass of 162 g/mole$^{-1}$ of a constitutive residue of dextran. It is assumed that each hydroxyl has the same reactivity and that the substitutions first affect each glucose unit once prior to a possible second substitution on the same residue.

A dextran T 40 of 40,000 g/mole$^{-1}$ thus contains 247 glucose residues of molar mass 162 g/mole$^{-1}$.

The substitution rates attained during the carboxymethylations are determined by acid-base determination with an automatic titrimeter (Tacussel). This determination finds a value $X_1$ corresponding to the number of moles of acid fixed per gram of polymer.

Thus, when a hydroxyl is substituted, there appears on the glucose a motif: —$OCH_2COONa$. Each of these substituted subunits has a relative molecular mass of 240 g/mole$^{-1}$.

Multiple motifs appear after sulfatation.

The rates of free carboxylic groups determined by acid-base determination gives a value $X_2$ which is always lower than the initial value $X_1$. The difference $X_1$-$X_2$ corresponds to the motifs —$OCH_2COO^-SO_3Na$. Each of these substituted subunits has a molecular mass of 320 g/mole$^{-1}$.

NMR analysis revealed that the S corresponds to a sulfatation of the free hydroxyls of the glucose residues in addition to the preceding reaction. In this case, a motif —$OSO_3Na$ appears. Each of these sulfated glucose subunits has a relative molecular mass of 200 g/mole$^{-1}$. The microanalyses provide the rates of S as a percentage of the mass of the polymer.

It is, therefore, possible at the end of synthesis to obtain the percentages of free carboxyl radicals $X_1$ and $X_2$ determined respectively before and after the sulfatation step, taking into account that the polymer contains:
  a unsubstituted glucose residues of mass 162 g.
  $X_2$ free carboxylic residues of mass 240 g.
  $X_1$-$X_2$ sulfated carboxylic residues of mass 320 g.
  Y sulfated glucose residues of mass 200 g.

Based on these data, it is possible to establish the percentage of substitution of the groups X and Y.

Thus, the percentage of sulfur provided by the microanalysis results (S %) make it possible to determine the number of atoms of sulfur ($\Sigma_s$) grafted on the polymer. This number of atoms is $\Sigma_s$=(S %×MM)/32×100, in which 32 is the atomic mass of S and MM is the molar mass of the synthesized polymer.

It is possible to obtain from this the percentage Y of radicals $SO_3$— as equal to: (100×S %×MM)/247×3200.

In the second case in which the grafted group Z is for example tyrosine, the same reasoning is applicable with the value of nitrogen given by the elemental analysis results.

B) Properties of the Polymers of the Invention

The properties that are common to the RGTA and the HBGFPP
  1) They are devoid of significant anticoagulant activity, i.e., they present an activity lower than 50 IU/milligram compared to that of heparin whose activity is on the order of 150 to 170 IU/milligram.
  2) They stabilize and potentiate the growth factors that present an affinity for heparin, particularly as examples $FGF_1$ and/or $FGF_2$ and/or TGFβ.
  3) They protect these factors against proteolytic agents such as trypsin.
  4) They inhibit the protease activities implicated in the inflammatory process such as for example leukocyte elastase or plasmin.
  5) They exert a cicatrizing effect in at least one of the models presented in the cited patents, i.e., the muscles, the nerves or the gastrointestinal tract.

The novel properties of the RGTA
  6) They protect and potentiate the enzymatic activities implicated in combating oxidative stress such as for example superoxide dismutase or SOD. Due to this property, they act as antioxidant agents and can be used alone or associated with SOD in the therapeutic and/or cosmetic indications of SOD or as an antioxidant protective agent especially in the protection of foods and nutrients.
  7) They inhibit the activity of enzymes such as calpaine.
  8) They inhibit the activity of enzymes such as heparitinase or heparinase.
  9) They increase the survival of cells subjected to ionizing radiation and regulate the secretion on both the quantitative and qualitative levels of the constituents of their matrix as well as the collagens for example.
  10) They act as antifibrotic agents by modulating the growth of the mesenchymal cells such as the smooth muscle cells, the fibroblasts or the hepatic cells and the quality of the type of collagen that they secrete.
  11) They present a slow degradability, a criterion which enables their differentiation from the heparan sulfates which are products that are naturally degraded by heparinase or heparitinase.
  12) They neither contain nor liberate after degradation products that are known to be toxic, such as for example can occur with the CMDBS with the grafted groups Z=benzylamine, which therefore rules out the CMDBS.
  13) They present in vivo capacities of protection and tissular regeneration in the following different models:
    a) cutaneous wound lesion,
    b) regeneration of osseous tissues such as the long bones, with the example of the femur,
    c) protection against the loss of osseous tissue and regulation of its reorganization such as in the case of osteoporosis or periodontal disease. They are, therefore, regulator agents of tissular homeostasis and of tissular masses such as osseous or muscular mass.
    d) hepatic regeneration or protection against the degeneration of the central and peripheral nervous systems,
    e) protection against the deleterious effects of ischemia regardless of its localization.

EXAMPLE 3

Measurement of the Anticoagulant Activities of the Polymers of Examples 1 and 2

The coagulation tests were performed using the Activated Cephalin Time technique or A.C.T. (Biggs, 1972, in: Human Blood Coagulation, Oxford Blackwell Scientific Publications). One hundred microliters of a polymer solution at different concentrations in Owen Koller buffer are incubated for 5 minutes at 37° C. with 100 microliters of plasma poor in platelets and 100 microliters of a solution of rabbit brain cephalin. 100 microliters of 0.25 M calcium chloride are added and the time until appearance of the coagulum is referenced by chronometry.

As shown in FIG. 11, the polymers of Examples 1 and 2 do not present anticoagulant activities greater than 50 IU/milligram, especially with respect to heparin which was used as a positive control. It should be noted that all of the values for the anticoagulant activities of the products presented here as examples are lower than 10 IU/milligram of product.

EXAMPLE 4

Stabilization and Potentiation of the Polymers of Examples 1 and 2 on Growth Factors Presenting an Affinity for Heparin and Particularly as Examples FGF 1 and/or FGF2 and/or TGFβ

This example considers the effect of the polymers on the stabilization of $FGF_1$ and the effect on the potentiation of FGF1 and FGF2. These effects are evaluated on the growth o.f 3T3 BALB/c or CCL39 cells. The conditions employed for these experiments are those described in the prior art in the patents relative to the HBGFPPs which are incorporated in the present invention by reference.

1) Effects of the polymers of the invention on the stabilization of FGF1 or FGF2

FIG. 12 shows the effects of the RGTA against thermal degradation at 20° C. and at 37° C. in relation to the incubation time of FGF2 conserved alone or in the presence of the tested products. The ED50 represents the concentration in micrograms/milliliter of FGF1, here 6 nanograms/milliliter, that must be inoculated in a culture of fibroblastic cells, the cells CCL 39, in order to obtain 50% of the maximum rate of incorporation of tritiated thymidine.

The results obtained show that all of the polymers tested exert at 20° C. as well as at 37° C. protective effects comparable to those of heparin, and with greater efficacy in some cases.

2) Effects of the Polymers of the Invention on the Potentiation of FGF1 or FGF2

The protocol is the same as described previously with a variable quantity of FGF possibly associated with a constant quantity of polymer. The concentration of polymer employed corresponds to that which potentiates to the maximum the mitogenic effect of the FGF. These tests are performed on 3T3 cells for FGF1 and FGF2. The controls are the same as those previously cited with the exception of a systematic determination for each test of the $ED_{50}$ value.

The molecules of these two families of tested polymers potentiate the actions of FGF1 and FGF2 because $ED_{50}$ values are obtained for FGF values that are lower or comparable to that obtained in the presence of heparin (FIG. 13).

EXAMPLE 5

Protection of the Factors Against Proteolytic Agents Such as Trypsin

Trypsin is a proteolytic enzyme with a broad spectrum of action which is used in in vitro tests and which is one of the primordial functional enzymes in the digestive process.

The test for protection against trypsin was therefore performed. One nanogram/final milliliter of iodinated $FGF_2$ or 5 micrograms/final milliliter of trypsin are incubated in a first step for 15 minutes at 37° C. with different concentrations of polymers (0.5 to 500 micrograms/milliliter) in a 100 mM Tris HCl buffer, 0.18 M NaCl, Brij 0.03% pH 7.6. Five micrograms/final milliliter of trypsin or 1 nanogram/final milliliter of iodinated FGF2 are then added respectively. The total rectional volume is 30 µl. The enzymatic reaction is stopped after 2 h of incubation at 37° C. by addition of Laemmli buffer and heating for 5 minutes at 90° C. (Laemmli U.K. Cleavage of structural proteins during assembly of the head of the bacteriophage T4, Nature, 1970, 227: 680-685).

Each sample is placed on a 15% polyacrylamide gel. Migration is performed for 1 h at 200 V in ice. The gels are dried for 2 h at 80° C. under vacuum and exposed at −80° C. in the presence of an autoradiographic film. The intensity of the bands is measured by image analysis and the percentage of FGF2 protected in relation to percentage of FGF2 degraded is calculated. Protection of FGF1 and TGFβ

FIG. 14 shows the protective effects expressed as % of protection of the poly-β-malic acid polymers on FGF1, FGF2 and TGFβ in relation to an attack by trypsin. FIG. 15 presents the protective effects expressed in % of protection of the polymers derived from dextran on FGF2 and TGFβ in relation to an attack by trypsin.

Most of these polymers exert a protective effect which is comparable to that of heparin which was used as positive reference.

EXAMPLE 6

Inhibition of the Protease Activities Implicated in the Inflammatory Process Such as for Example Leukocyte Elastase or Plasmin Leukocyte elastase and plasmin are key proteases in the installation and unfolding of the inflammatory tests. These tests are intended to establish whether the polymers protect the growth factors from degradations by human leukocyte elastase.

The tests for protection against leukocyte elastase are therefore performed. The protocol employed is the same as that used with trypsin with 30 nanograms/final milliliter of elastase and 0.5 to 500 micrograms/milliliter of polymers. The buffer is 100 mM Tris HCl, 0.18 M NaCl, 0.03% Brij pH 8. The intensity of the bands is evaluated by image analysis and the percentage of nondegraded FGF2 is calculated. The positive control for these tests is heparin. Dextran T40 and dextran sulfate were used as internal references.

FIG. 16 presents the inhibitory effects of the different polymers expressed by their $IC_{50}$ values.

EXAMPLE 7

Example of the Effects of the RGTA on the Regeneration, Protection and Functional Restoration of the Tissues: Case of the Regeneration of Skeletal Muscle The model employed for evaluating most effectively the cicatrizing properties of the RGTA was that of the crushed muscle as defined and presented in French Patent No. 2 718 026.

After crushing the EDL (Extensor Digitorum Longus) of the rear paw of the rat and injection of the crushed muscle into a solution of physiological serum containing or not containing the test substances, the muscles treated in this manner are recovered 8 days after the operation. Analysis of the weights as well as a histological study make possible quantification of the effects of the polymers on muscular regeneration. The results are expressed in % in relation to the characteristics of a muscle that only received an injection of the physiological serum without polymer under the same experimental conditions. FIG. 17 presents the results obtained which demonstrate that the new polymers derived from the dextran skeleton as well as the copolymers of β-malic acid exert the claimed effects.

It is important to note that these effects on muscular regeneration are obtained not only by in situ injection of the polymers but also by intravenous, intra-arterial or intramuscular injection as long as the doses injected are selected in relation to the routes of administration.

EXAMPLE 8

Effects of the RGTA on the Regeneration of Flat Bone

The model employed for evaluating the cicatrizing properties of the RGTA is the method already known in the prior art and described by Blanquaert F, et al., Bone, 1995; 17(6): 499-506.

This model comprises performing a circular trepanation of 5 millimeters in diameter in the calvaria of an adult rat. The defect is filled with a collagen buffer that has been cut to the same dimensions and impregnated with or not impregnated with a solution containing the RGTA. In the example presented here, the polymers studied are the type CMS polymers (RGTA 1005 and 1012) and the β-malic acid copolymers (RGTA 2011). Table III below presents the percentages of osseous filling established by image analysis of the radiographs taken 35 days after treatment.

TABLE III

| Type of treatment | % of osseous filling |
|---|---|
| control | 18 ± 4.8 |
| RGTA 2011 | 56 ± 7.0 |
| RGTA 1005 | 54 ± 6.9 |
| RGTA 1012 | 72 ± 8.9 |

Thus, both types of polymers stimulate osseous regeneration since under the cicatrization conditions the sagittal suture forms ad integrum.

EXAMPLE 9

Protection and Potentiation of the Enzymatic Activities Implicated in Combating Oxidative Stress Such as for Example Superoxide Dismutase or SOD The production of $O_2^-$ ions and that of hydrogen peroxide ($H_2O_2$) represent radicals that exert especially destructive cytotoxic effects. SOD or superoxide dismutase are enzymes engaged in the detoxification of these radicals. They are agents that preserve the organism from oxidative stress.

The RGTA present various types of activity in relation to SOD:
They exert a potentiating effect on the catalytic activity of SOD at neutral pH and a protective and potentiating effect at acid and basic pH values.
They present the property of protecting SOD in relation to enzymatic degradations such as for example trypsin and also in relation to heat treatment.
On models of activated monocyte cultures, they stimulate the catalytic activity of the endogenous SOD and enable diminishment of the production of the superoxide ions.

In all cases, the quantitative determination of SOD activity is performed using Pick's technique (Freund M and Pick E, The mechanism of action of lymphokines. IX. The enzymatic basis of hydrogen production by lymphokine-activated macrophages. J Immunol 1986, 15; 137(4): 1312-1318). This technique is based on the determination of the $O_2^-$ ions by reduction of cytochrome c. MnSOD (Sigma ref. S 8151) at 30 U/milliliter is dissolved in the presence of different RGTA at the concentration of 10 micrograms/milliliter. These mixtures are subjected to different treatments.

The SOD activity is evaluated in the presence of different concentrations of polymers under normal rectional conditions.

The mixtures of SOD and polymers are either subjected at room temperature to the action of trypsin (same conditions as for the protection tests of Example 5) or they are subjected to thermal treatment at 60° C. for 30 minutes. The residual catalytic activity of the SOD of these mixtures is then evaluated by conventional enzymatic techniques or on a cellular system.

The samples treated in this manner are incubated in a suspension of monocytes (2.5·106 cells/milliliter) stimulated by 200 nM of PMA. This condition induces the production of superoxide anion by these monocytes activated into macrophages. The stimulation by PMA induces an increase in the production of superoxide ions normally produced at a basal level in the absence of activation. The addition of active MnSOD used as positive control diminishes the quantity of superoxide ions produced.

Under these conditions, the lower the production of superoxide ions, the higher will be the residual catalytic activity of the SOD contained in the mixtures. Thus, these tests make it possible to evaluate the protective and potentiator effects of the polymers on the activity of exogenous as well as endogenous SOD.

Figure 20:
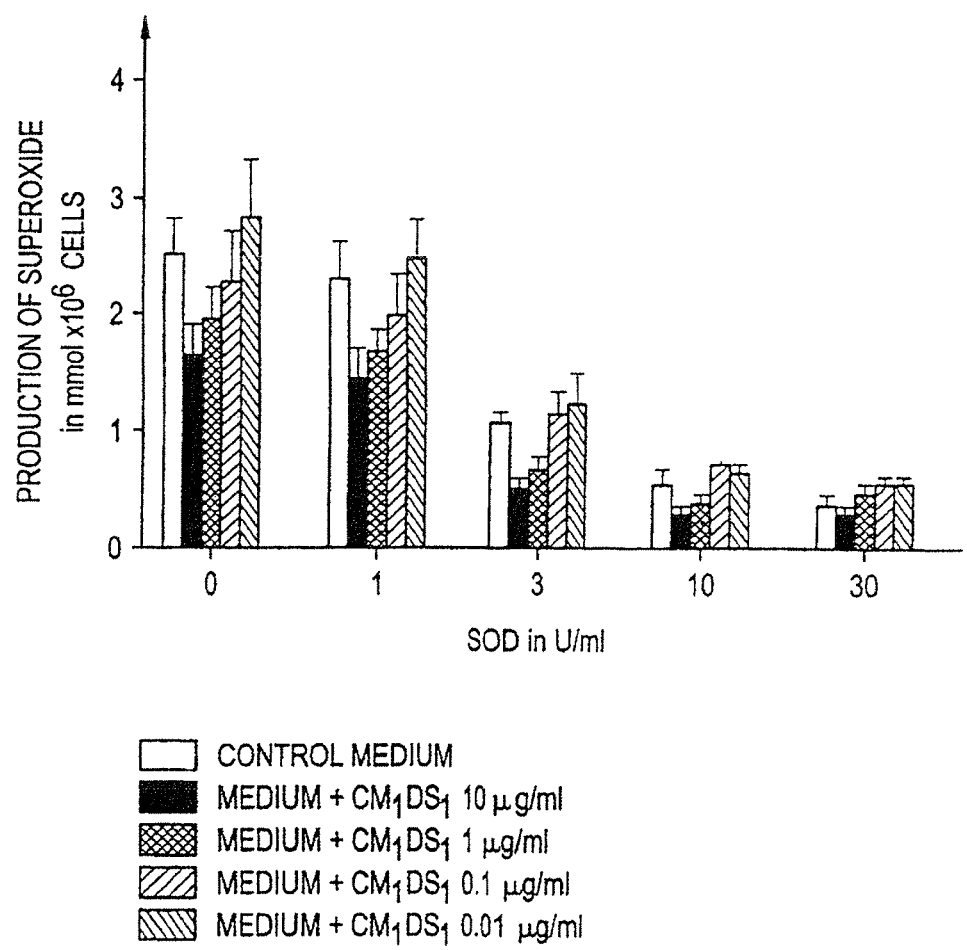
FIG. 20 is a graph showing the potentiation effect of SOD produced in vitro by activated monosites.

FIG. 18 illustrates the protective and potentiator effects of the RGTA on the catalytic activity of SOD in vitro at different pH values. FIG. 19 illustrates the protective effects of the RGTA on SOD subjected to an attack by trypsin or after a thermal shock. FIG. 20 illustrates the potentiator effects of the SOD activity on the production of superoxide ions by the activated macrophages.

Conclusion: Thus, the polymers exert potentiator and protective effects in both acellular and cellular systems. Thus, the addition of different polymers modulates the catalytic activity of SOD added endogenously as well as SOD produced endogenously by the cells.

EXAMPLE 10

Inhibition of the Activity of Enzymes Such as Calpaine by the RGTA

1) Introduction
Calpaine 1 (Sigma P 4533) is used in this example. Thus, 0.78 enzyme unit (57.2 nM) are incubated in 1 milliliter of 50 mM Tris-HCl buffer, pH 7.4, 0.5% Brij, 2 mM $CaCl_2$, 2 mMDT and 0.15M NaCl. The RGTA solutions to be tested are added over 5 minutes at 27° C. The substrate (250 micromolar of N-succinyl-leu-tyr-amido-7-methyl coumarin, from Sigma (S 1153) is then added to a quartz tank to which the mixture described above is then added. Measurements are then performed every 3 to 5 minutes by excitation at 380 rim and detection in fluorescence at 460 rim of the transformation of the substrate into 7-amino-4-methyl coumarin (according to the protocol described by Sasaki, Kikuchi, Yumoto N, Yoshimura and Murachi T, 1984, in J. Biol. Chem. 259 (20), p 12489-12494).

The results obtained are summarized in FIG. 21.

2) Conclusion
We can predict from the results obtained in the inhibition of the activity of calpaine by the RGTA that the RGTA have a protective activity against the lesions induced by cerebral ischemia as could be anticipated from the publications of Markgraf C G et al. (Stroke, 1998, 29, 152-15.8) or Saido et al. (Neuroscience Letters, 1997, 16; 227: 75-78) which describe the effect of calpai.ne inhibitors such as MDL28170 or the protein calpastatine in the treatment of postischemic lesions of the cortex or hippocampus. Administration of RGTA via the local or intravenous route has the effect of inhibiting the calpaines and promoting the repair of the nervous tissue which has been injured especially by lack of oxygen supply as is the case in ischemia.

EXAMPLE 11

Inhibition of the Activity of Enzymes Such as Heparitinase by the RGTA a) Inhibitory Activity of Heparinase and Heparitinase
Measurement of the inhibition by the RGTA of heparinase or heparitinase activities is performed using as substrate heparan sulfates radio-tagged with sulfur 35 and present in an extracellular matrix synthesized by endothelial cells cultured in the presence of Na2 35SO4 for 7 days. The protocol used is the one described by Ishai-Michaeli R et al. (Importance of size and sulfation of heparin in release of basic fibroblast growth factor from the vascular endothelium and extracellular matrix. Biochemistry 1992; 31(7): 2080-2088). The extracellular matrix obtained after elimination of the endothelial cells is then incubated for 24 .h at 37° C. in the presence or absence of heparinase and 0.5 microgram/ml of RGTA. The incubation medium is collected and deposited on a Sepharose 6B column in accordance with the protocol described in Ishai-Michaeli (Biochemistry 1992; 313(7): 2080-2088) to measure the degradation of radio-labeled heparan sulfates. FIG. 22 illustrates the results obtained. The heparan sulfates of high molecular weight corresponding to the material not degraded by the enzyme heparinase were eluted first (fractions 3 to 20). The heparinase treatment caused the disappearance of this peak and the appearance of a peak corresponding to low molecular weight fractions of degraded heparan sulfates (fractions 20 to 40). In the example presented, the effect of RGTA 1005 at 50 micrograms/ml induces 50% inhibition and 100 micrograms/ml induces 100% inhibition of the heparinase activity.

EXAMPLE 12

Effects of the RGTA on the Protection of Human Intestinal Smooth Muscle Cells Subjected to Ionizing Radiation; Effects on their Survival and on their Anti Fibrotic Effects Evaluated by Means of the Quantity and Quality of the Secreted Collagens The formation of a fibrous or fibrotic tissue is an essential physiological step associated with the processes of tissue repair and restructuring. The fibrotic tissue is a filling tissue, normally transitory, intended to conserve the structural and functional integrity of the tissues and organs. It is characterized by its richness in collagens of the extracellular matrix.

When this condition persists or develops, it corresponds to a pathology that illustrates a disturbance of the structural and functional homeostasis of the tissues and is manifested by an abnormally high accumulation of extracellular matrix which generates a fibrosis. A fibrosis, regardless of its origin, is characterized by:
the presence of a permanent inflammatory infiltrate, the existence of a disequilibrium in the balance between a proliferative and a quiescent state of the conjunctival or mesenchymal cells such as fibroblasts or smooth muscle cells, the progressive destruction of the invaded tissue which is renewed only slightly or in a defective manner, the existence of a disequilibrium of the balance between the synthesis and the degradation of the extracellular matrix.

A fibrosis can be induced either subsequent to a trauma of various origins (infectious, mechanical, toxic, etc.) or subsequent to ionizing radiation (notably by γ rays). In this case, we are dealing with radioinduced fibroses as is frequently the case in patients undergoing radio-therapy.

The collagens are the major components of the extracellular matrix of normal tissues as well as of fibrotic tissues. The collagens are essentially synthesized by the mesenchymal cells such as the fibroblasts and the smooth muscle cells. In a fibrous tissue, the total collagen is quantitatively increased due to reasons affecting on both the quantitative and qualitative levels the synthesis and/or degradation of the collagens, i.e., the dynamic of the restructuring. Fibroses are characterized by an increase in type III collagen, with this taking place preferentially in the case of radioinduced fibroses. This increase in type III collagen is associated with an increase but to a lesser degree in the ratio between type III collagen and type I collagen. Another collagen, type V collagen, is associated with the quality of the organization of the collagen fibers in the matrix, i.e., the fibrillogenesis. In fibrotic tissues, the decline in the levels of type V collagen is one of the origins of the loss of structure of the collagen fibers of the extracellular matrix.

The cellular model employed in this example is that of HISM cells, Human Intestinal Smooth Muscle cells (American Type Culture Collection, Rockville, Md. ATCC CRL 192), stemming from the muscularis propria of human jejunum (Graham M., Diegelmann R., Elson C., Bitar K. and Ehrlich H., Proc. Soc. Exp. Biol. Med. 176 (1984) 503). This line of human intestinal smooth muscle cells was used to evaluate the effects of radiation on cellular survival and the induction of fibrotic phenomena analyzed by means of the quantity and quality of the types of collagen secreted by these normal cells or in an inflammatory situation or in the repair process by a fibrosis.

The cells are cultured in DMEM medium containing 1 g/l of glucose, 1% of L glutamine, 1% penicillin-streptomycin and 10% of fetal calf serum and conserved in an incubator at 37° C. under an atmosphere saturated at 5% $CO_2$ and 95% relative humidity, in 75-$cm^2$ plates. The HISM cells are seeded on plates with 24 flat-bottom wells at the rate of 20,000 cells per well. The volume of each well is brought up to 2 milliliters of medium. Various growth kinetics are implemented in the presence or lack of presence of RGTA at different concentrations ranging from 0.4 to 400 micrograms/milliliter.

Irradiation is performed from a $^{60}$cobalt irradiation source in an incubator in which the culture plates are arranged. Two plates are subjected simultaneously to this irradiation the source of which is vertical and the doses are evaluated in relation to the surface irradiated. The irradiator flow rate is 1 Gy/min. The doses absorbed are 10 Gy for an irradiation time per plate of 10 minutes.

Different protocols are used to evaluate the role of the RGTA depending on whether they are added to the culture medium before, during or after the irradiation, i.e., at the preventive or curative level, or both at the same time. Table IV below provides more specific information on the different protocols.

TABLE IV

| Sequence | RGTA | Irradiation | RGTA |
|---|---|---|---|
| Control | — | — | — |
| Irradiation | — | 0 | — |
| Curative | — | 0 | 0 |
| Preventive | 0 | 0 | — |
| Preventive and curative | 0 | 0 | 0 |

The preventive effect is evaluated by addition of RGTA (+) at the dose of 400 micrograms/ml in the culture medium 48 hours prior to the irradiation. The curative effect is evaluated by addition of RGTA 2 hours after irradiation at the same doses as for the preventive effect. For the cumulative preventive and curative effects, the cells are continuously cultured in the presence of the same doses of RGTA.

72 hours after the irradiation, the cells are incubated in a medium free of serum in the presence of tritiated proline (10 microCi/ml) and ascorbic acid (50 micrograms/ml) for 24 hours. The supernatant is then collected and the cellular layer is recovered using a robber-policeman in a final volume of 18 ml. The culture media and the recovered cellular layers are extensively dialyzed (cutoff threshold of 6 to 8 kDa) against flowing water (24 hours at 4° C.) to eliminate the small molecules from the macromolecules. After dialysis, aliquot fractions are collected and hydrolyzed (6M HCl, 105° C., 24 h) for determination of the radioactivity of the hydroxy($^3$H) proline, specific marker of the collagens. At this stage, an aliquot fraction is used for quantification by counting of the radioactivity of the total synthesis of the collagens.

The remaining volume is dialyzed again in the presence of pepsin and collagen I against 0.5 M acetic acid for 24 h at 4° C. The pepsin will digest the noncollagenic contaminants which will be eliminated in the dialysate in the form of peptides. Type I collagen is added to augment the proportion of collagen which is low in each sample and to trend towards an enzyme/substrate ratio of 1:5. The reaction conditions are as follows: 1 ml of pepsin solution (0-5 M)+1 ml of solution of collagen I (0.5 M)+0.514 ml of acetic acid to have a final concentration of acetic acid of 0.5M in an 18-ml sample. Each dialysate obtained in this manner is lyophilized in the cold state (−50° C.) and conserved at −20° C. until use.

The different collagen a chains are separated by polyacrylamide gel electrophoresis in the presence of SDS (Sodium Dodecyl Sulfate) in accordance with Leammli's method, after reduction with β-mercaptoethanol. The radioactivity incorporated in each collagen is determined by hydrolysis of the α chains obtained by cutting off the gel bands corresponding to each collagen chain of a specific type. These bands are then dissolved in oxygenated water at 60° C. and the radioactivity contained in the different dissolved bands is counted with the liquid scintillation β counter or by direct autoradiography on the gels.

The electrophoretic separation is performed with 5 microliters of collagen V and 50 microliters of each reduced sample.

These gels allow various types of processing:
Determination of the different types of collagen by analysis of the incorporated radioactivity.
Quantification of these different types of collagen by densitometric analysis after autoradiography.

The aliquot fractions collected after the dialysis against flowing water are hydrolyzed (6M HCl, 105° C., 24 h) in sealed ampoules. The acetic acid is then evaporated, and then the content of the ampoule is resuspended in 1 ml of distilled water. The proline and hydroxyproline are separated by the method of Rojkind and Gonzales (Rojkind M and Gonzalez B, An improved method for determining specific radioactivities of proline-14C and hydroxyproline-14C in collagen and noncollagenous proteins. Analytical Biochemistry 1974; 57(1): 1-7). The principle is based on oxidizing the proline and hydroxyproline with chloramine T. The proline is transformed into pyrroline carboxylate which is soluble in toluene whereas the hydroxyproline is transformed into water-soluble carboxylate. After treatment, the proline and hydroxyproline fractions are recovered for each sample and quantified by measurement of the radioactivity.

Figure 23:
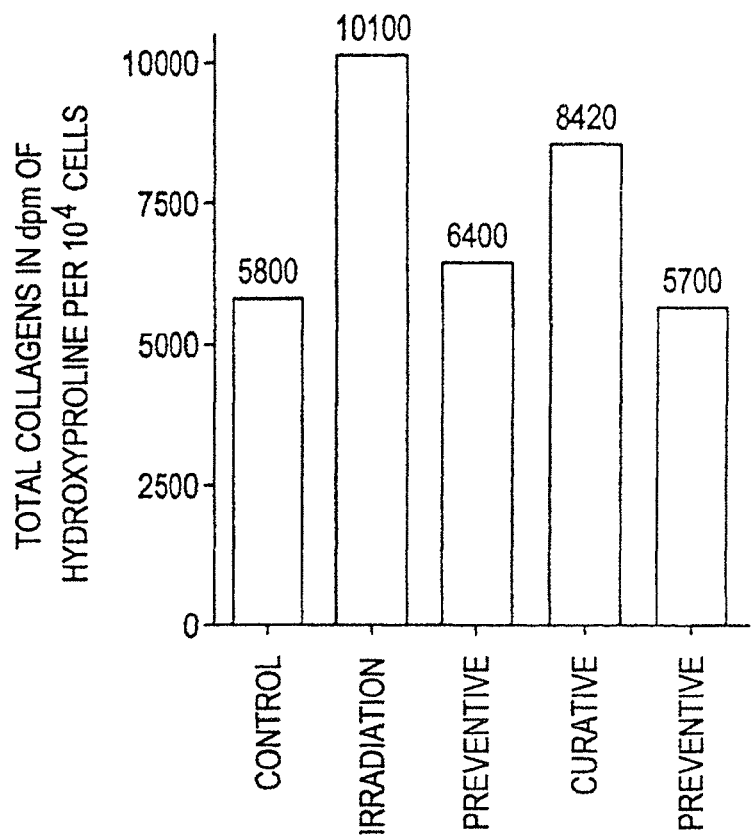
FIG. 23 is a graph showing the actions of selected polymers of the invention on the secretion of cologens in vitro by HISM cells subjected to ionizing radiation of $^{60}$Co.
Figure 24:
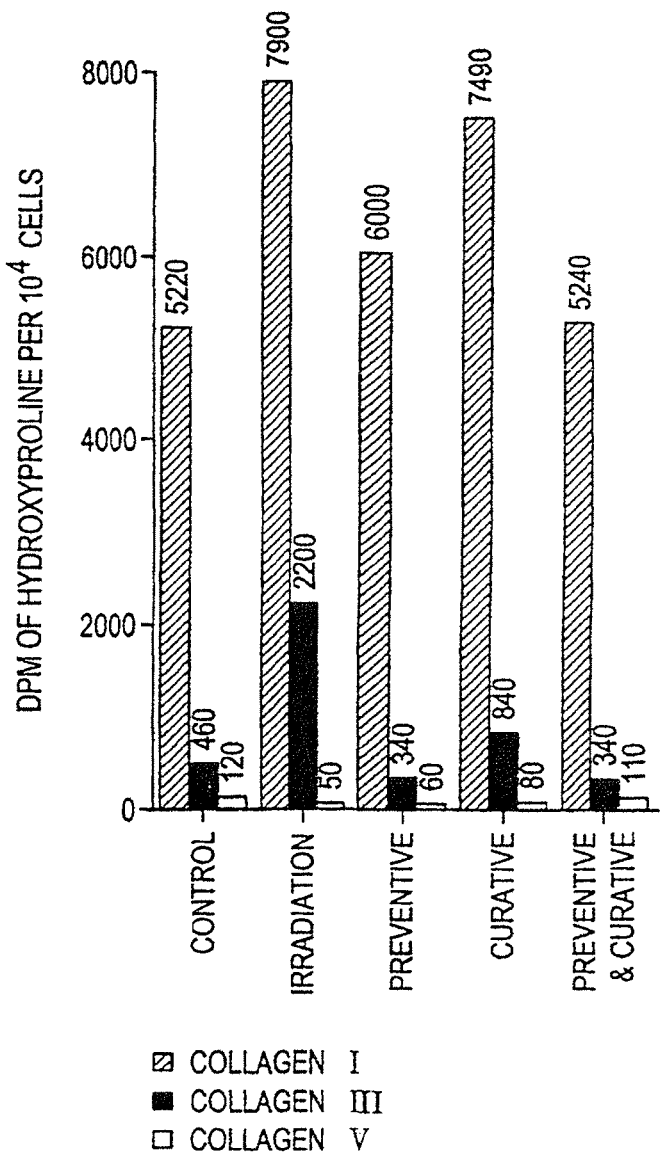
FIG. 24 is a graph showing the action of selected polymers of the invention on the synthesis of Type I, II and V collagens by HISM cells subjected to ionizing radiation of $^{60}$Co.

Under normal conditions, the HISM cells are characterized by the quantity of collagen synthesized (FIG. 23) and especially on the qualitative level by the phenotype of the collagens secreted (FIG. 24).

Under normal conditions, the collagen that comprises the majority of the collagen is type I collagen. Type III and type V collagens are present in smaller proportions. The quantity of type V collagen is associated with the quality of the organization of the fibrillogenesis.

Type III collagen is a "warning" collagen, theoretically synthesized in a transitory manner in the case of reaction to a stress but in a permanent manner in the case of a fibrosis. The proportional quantity of type III collagen in relation to type I collagen increases in a noteworthy manner in situations involving response to a tissular lesion, stress or aggression such as for example ionizing radiation. Type III collagen becomes preponderant in the matrices of tissues presenting an acute as well as a chronic fibrotic reaction. This collagen can be considered to be a signaling component of the fibrotic reaction.

When the HISM cells are cultured under control conditions, i.e., without RGTA, they synthesize these three types of collagen (FIG. 24). Irradiation modifies the quantity (FIG. 23) and the quality (FIG. 24) of the collagens produced. The overall synthesis of collagen increases by close to 50% (FIG. 23). Secretion of this type I collagen and especially of type III collagen increases considerably (respectively by 50% and close to 500%). In contrast, synthesis of type V collagen diminishes by more than 50%.

The presence of different RGTA (RGTA 1005 and RGTA 1025) restores almost exactly the control behavior of the cells despite their exposure to the irradiation. FIG. 23 shows that the overall synthesis of collagen returns to normal values especially for the conditions of preventive or cumulative (preventive+curative) treatments. FIG. 24 confirms this return to a reference homeostasis especially in the case of cumulated treatments. The curative as well as the preventive treatments exert the same types of effects, especially with regard to the values of the ratios of secretion of type I and type III collagens which return to values comparable to those of the control cells. These RGTA restore the functioning of the HISM cells in relation to the collagens.

Figure 25:
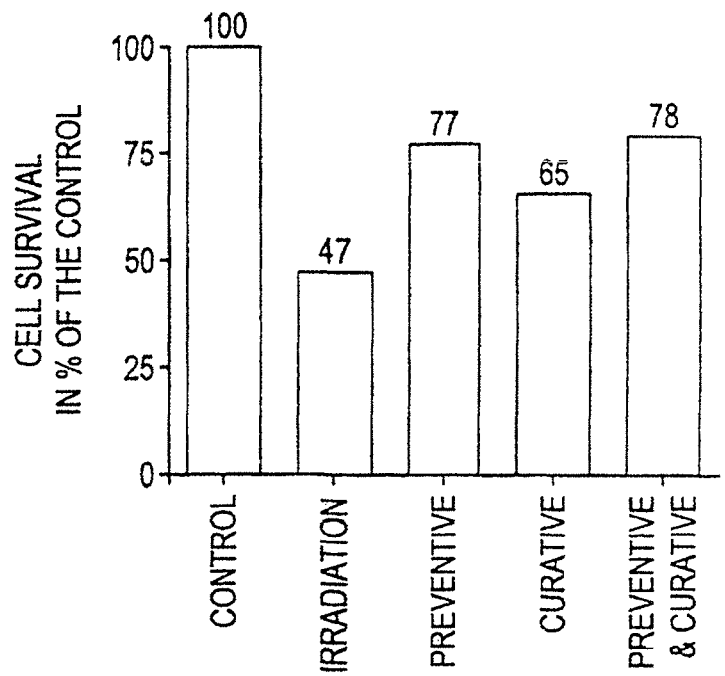
FIG. 25 is a graph showing the protective effects of selected polymers of the invention on the survival of cells subjected to $^{60}$Co irradiation.
Figure 27A:
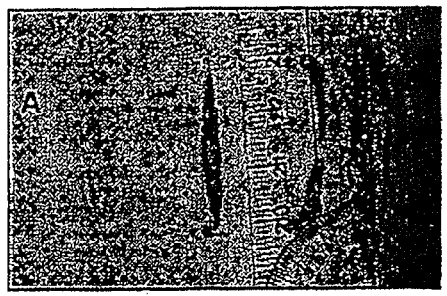
FIGS. 27A-27D is a series of photographs showing the effects of polymers of the invention on cutaneous cicatrization.
Figure 27B:
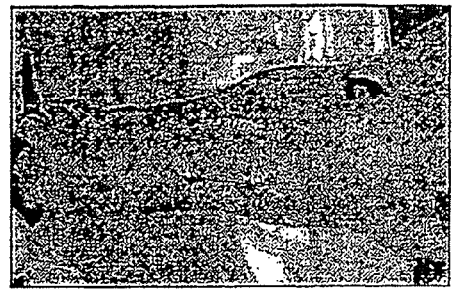
Figure 27C:
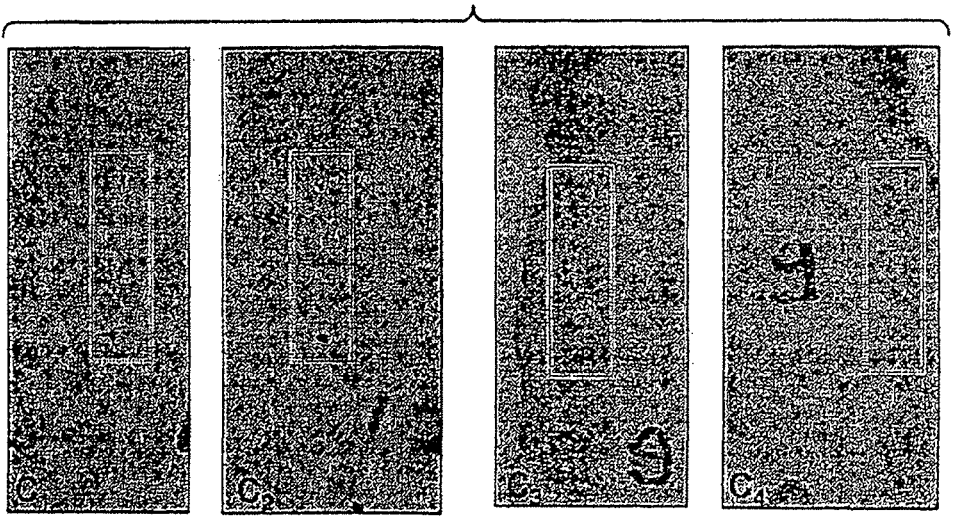
Figure 27D:
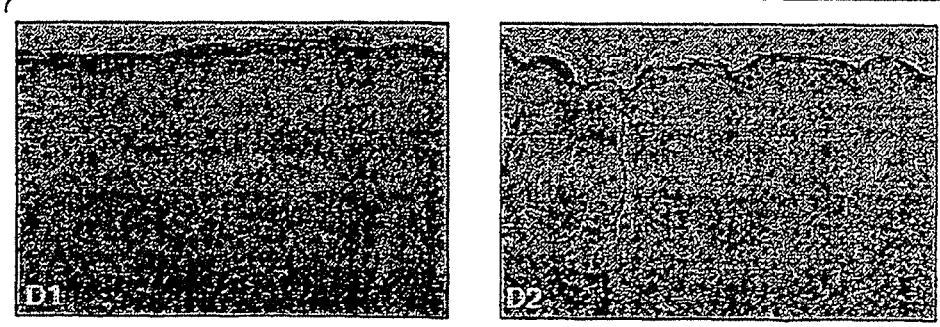

The RGTA also act on the survival of the cells (FIG. 25). In fact, irradiation induces a high cellular mortality rate of more than 50% of the irradiated population. In the presence of the polymers, a clear protective effect is recorded because the mortality rate is reduced to approxi¬mately 25%, with the most pronounced effect being obtained for the cumulated preventive+curative treatments.

EXAMPLE 13

Action as Antifibrotic Agents in Modulating the Growth of Mesenchymal Cells Such as Smooth Muscle Cells, Fibroblasts or Hepatic Cells and the Quality of the Type of Collagen that they Secrete As discussed in example 12 above, fibrosis manifests an alteration in growth of the mesenchymal cells associated with a modification of the quantity and quality of the collagens synthesized.

This example uses another cellular model which comprises smooth muscle cells from the pig aorta. These cells are obtained by means of the aorta explant method. The aorta is composed of three cellular layers: the adventitia (external layer) which contains the fibroblastic cells, the media (central layer) which contains the smooth muscle cells (SMC) and the intima (internal layer) which contains the endothelial cells.

The media is removed and torn up into tiny pieces. The explants are cultured on a 25-cm$^2$ plate containing DMEM 1 g/l of glucose with phenol red, with the addition of 20% of fetal calf serum (FCS), 1% of L-glutamine and 1% of penicillin-streptomycin. The cells become detached from these explants and colonize the medium (stage P0). Two weeks after the beginning of the culture phase, the cells are congealed at a cellular density of 2 million cells in 10% DMSO and DMEM 20% FCS.

The growth kinetics are determined by evaluating the number of cells per well by means of an automatic particle counter (Coulter Counter ZM, Coultronics) which was previously calibrated by an evaluation of the cell diameter by means of a Malassez cell. Each counting was performed on an average of 4 wells from which the cells were detached by means of 500 microliters/well of a trypsin-EDTA (10 mM) solution.

The smooth muscle cells were seeded under the same experimental conditions as the HISM cells. The growth kinetics were determined in the presence of or lack of presence of polymers of the series RGTA 1000 to 1025 for the polymers in which Z is nothing, and of the series RGTA 1110 to 1115 for the polymers in which Z exists, and of heparin as control, at different concentrations ranging from 0.4 to 400 mg/ml.

The percentage of inhibition of the proliferation is calculated according to the following formula:

$$I\% = 100 \times (1 - \text{net growth with polymers/net control growth})$$

in which net growth represents the difference between the quantity of cells counted when they merge with the number of cells seeded at the beginning of culturing.

The control corresponds to the smooth muscle tissue cultures in the absence of polymers. Heparin and the RGTA represent the different effectors tested which are capable of modifying the biological activity of the cell.

Under the same conditions as employed for the HISM cells, the synthesis and typing of the collagen by the smooth muscle cells was determined.

FIG. 26 shows the results obtained. The RGTA exert an inhibitory effect on the proliferation of the smooth muscle cells which is comparable to that of heparin which was used as control reference molecule. This effect can be seen from the values in the two first columns. However, and in contrast to heparin, these polymers reestablish the collagen secretion phenol-type. In summary, the overall synthesis rate of collagens is significantly diminished in the presence of RGTA 1005, 1012 and 1013. At the qualitative level, these same polymers, again in contrast to heparin, diminish the rate of synthesis of type I and type III collagens while increasing the secretion of type V collagen.

These effects confirm the antifibrotic properties of the polymers of the invention.

EXAMPLE 14

Effects of the RGTA on Regeneration of the Skin in the Rat

This example illustrates the effect of the RGTA on deep cutaneous cicatrization after suture in the rat.

Male Hairless rats weighing 250 grams were anesthetized by an IM injection of ketamine and Largactil. Two 3-cm excisions were made laterally in relation to the dorsal axis of symmetry of the animals on each side of the spinal column (FIG. 27). In relation to the control animals which were not treated with RGTA 1012, the treated animals received via the intramuscular route an injection of a solution of RGTA 1012 at 1 milligram per kilogram 30 minutes prior to the excision and 100 microliters of a solution at 100 micrograms per milliliter as topical application on the wound just prior to suturing. The suture was performed in a single plane with an intradermal continuous suture with Prolene 2-0. The treated rats and the control rats were macrophotographed on days 7, 21 and 60 after the operation. At each of these time points, three rats from each experimental series were euthanized so as to be able to perform a histological study of the cutaneous cicatricial samples.

FIG. 27 shows the effects of the RGTA on the cutaneous cicatrization:

FIG. 27-A: Deep cutaneous incision performed down to the subjacent muscular floor, 3 cm long, on both sides of the spinal column.

FIG. 27-B: Dorsal view of the animal after suturing of the wound edges by continuous suture.

FIG. 27-C: Appearance of the cicatrices ten days after the treatment. C1 and C2 correspond to a control animal treated with physiological serum without RGTA 1012. In C1 the threads have not been removed in contrast to photograph C2. The cicatrix is visible and still presents scabs of coagulated blood especially where traces can be seen of the needles used for the suture. C3 and C4 correspond to an animal treated with physiological serum containing RGTA 1012. At the same time, the cicatrices are no longer visible. The suture threads are visible in figure C3 whereas they were removed in figure C4. In this photograph, only a fine border marks the original incision.

FIG. 27-D: Histological analysis. D1 and D2 present the histological sections of the skin that was incised 60 days earlier. D1 corresponds to a control animal that was treated with physiological serum without RGTA 1012; figure D2 corresponds to an animal treated with physiological serum containing RGTA 1012. In D1, the dermis subjacent to a still imperfectly mature epithelium has not returned to a structure identical to that of normal skin. The restructuring is very partial. The opposite is true of D2 in which the skin has returned to a structure and an organization identical to that of skin that was never injured. The only trace of a cicatrix is visible in the depth of the dermis where an incompletely restructured zone can be detected. In this later case, there is complete absence of external cicatrix.

The photographs of FIG. 27 show at the end of 7 days the disappearance of the superficial cicatrix whether the threads had (C4) or had not (C3) been removed whereas in the control animals a cicatrix can be seen under both of these conditions (C1 and C2).

A histological analysis performed at 60 days revealed that the skins of the untreated animals (D1) presented a dermis that was absolutely not mature whereas the animals treated with the RGTA revealed only a slight dermal trace at the deep level. The histology of the skin of the treated animals (D2) has an appearance comparable to the skin of a control animal not subjected to any cicatricial processes whatsoever. In this model, the RGTA not only accelerate the cicatrization rate of the cutaneous floor but also and especially enable a restoration of the cicatricial tissue which results in a regenerated tissue in which no trace of fibrosis can be detected. This example shows that the RGTA are especially powerful regulators of tissular homeostasis.

EXAMPLE 15

Protective Effects Against Ischemia Manifested by the RGTA

Figure 28A:
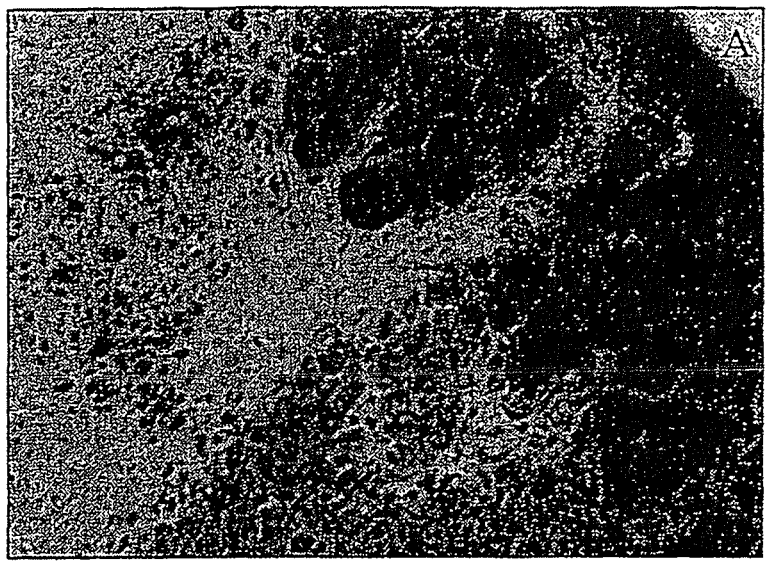
FIGS. 28A-28B is a pair of photographs of the protective effects of polymer RGTA 1005 against tissue injury in a muscle ischemia model in a rat.
Figure 28B:
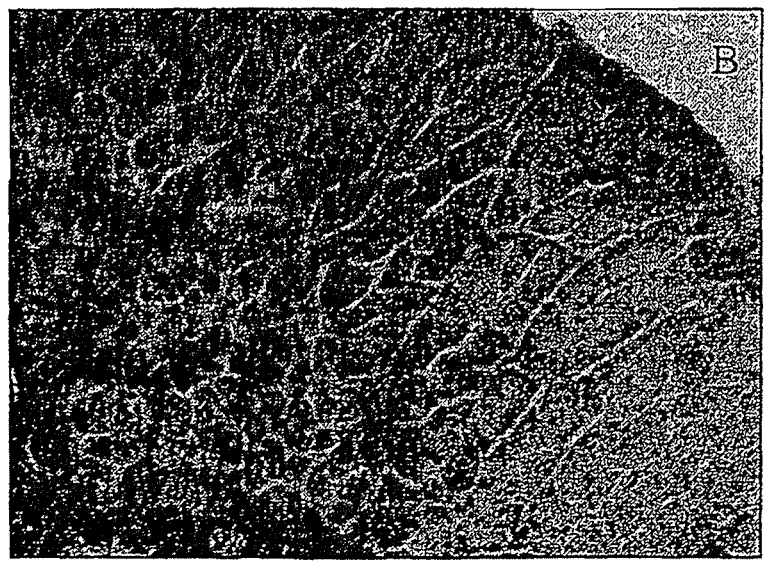
Figure 29A:
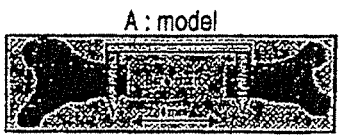
FIGS. 29A-29J is a series of photographs showing the effects of a polymer of the invention RGTA 1015 on the regeneration of long bones and histological and radiographic studies of femurs from rats which were treated or not treated.
Figure 29B:
Figure 29C:
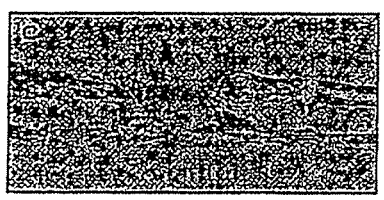
Figure 29D:
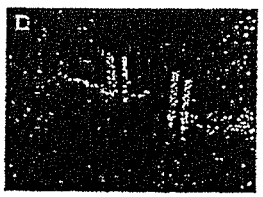
Figure 29E:
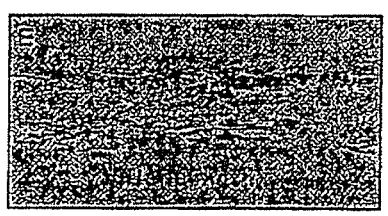
Figure 29F:
Figure 29G:
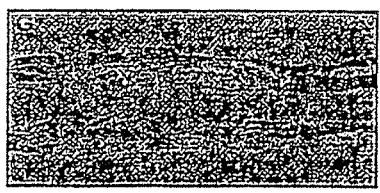
Figure 29H:
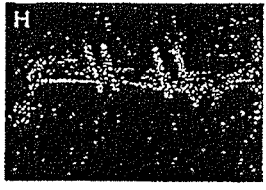
Figure 29I:
Figure 29J:
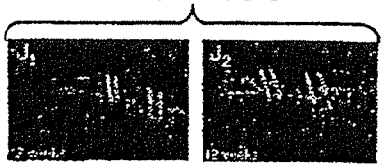

This example demonstrates, using the polymer RGTA 1005, the protective effects of the RGTA against tissular damage which enabled conservation of 80% of the mass of an organ compared to the untreated organs (FIG. 28). These protective effects of the RGTA against the deleterious effects induced by the stress caused by a lack of oxygen supply stemming from an ischemia of the muscles are presented in the experimentation described below.

The model employed is inspired by the model described by Hansen-Smith, F. M., Carlson, B. M. & Irwin, K. L. (1980, Revascularization of the freely grafted extensor digitorum longus muscle in the rat. *Am. J. Anat.* 158, 65-82). The experimental procedure consists of sectioning the neurovascular trunk of the EDL muscles (Extensor Digitorum Longus) on the two rear paws of adult Wistar rats (350 g) at the level of its entry in the muscle and of completing the ischemia by a ligature of the two tendons. An injection of 100 microliters of an RGTA 1005 solution at 50 micrograms per milliliter in physiological serum was then made directly into an EDL muscle. The same volume of physiological serum without RGTA was injected into the other contralateral muscle.

Seven days after the injection, the muscles were removed and examined with a microscope after histological preparation. In each group of treated or untreated muscles, groups of parameters such as the mean diameter of the muscle, the thickness of the epimysium, of the peripheral zone and the mean diameter of the ischemic zone were measured using a 10× objective and a micrometric scale. The number of layers of muscle fibers that survived the ischemia in the peripheral zone was counted in thirty different fields selected at random and observed with a 20× objective.

FIG. 28 shows the protective effects of the RGTA (RGTA 1005) against tissue injury in a muscle ischemia model in the rat. FIG. 28-A and FIG. 28-B show, respectively, histological muscle sections from a control rat (28-A) and from a rat treated (28-B) with a solution of RGTA 1005. In the control, the ischemia caused the degeneration of the muscle fibers with the exception of a corona of peripheral fibers in contact with the epimysium. Administration of RGTA 1005 limits to a considerable degree the degeneration of the deep muscle fibers just as it diminishes in a very significant manner the inflammatory reaction and the degradation that this reaction induces. Thus, RGTA 10015 protects the cells from the deleterious effects induced by ischemia.

It can be seen in FIG. 28 that after one week, the mean diameter is unchanged after treatment with RGTA (5.2±0.3 mm) compared to the diameter (5.1±0-2 mm) of an uninjured control muscle. The inflammatory reaction in the epimysium is diminished in the muscles treated with the RGTA in a very significant manner since the thicknesses of the epimysia are 10±5 micrometers with treatment by the RGTA compared to 85±10 micrometers without treatment with the RGTA ($p<0.01$). The central ischemic zone of the EDL muscles not treated with RGTA presents a mean diameter of 4.4000±100 micrometers in which the muscle fibers have completely disappeared. This zone is surrounded by a peripheral zone of 270±50 micrometers containing an average of 3.2±0.5 layers of muscle fibers. The treatment with the RGTA is characterized by a clear decrease in the size of the central degenerated zone whose mean diameter is 300±200 micrometers ($p<0.05$) and an augmentation of the peripheral zone the thickness of which is 700±40 micrometers ($p<0.05$) and which contains 8-3±1.8 layers ($p<0.01$) of fiber.

EXAMPLE 16

Effects of the RGTA on the Regeneration of Long Bone

This example illustrates the reconstruction of an osseous defect created in the diaphysial shaft of a rat femur, restored to the original state after 8 weeks and better at 12 weeks, with reconstitution of a medullary cavity identical to the original one and mature cortices as in the original unfractured bone (FIG. 29).

Male Wistar rats (Ico: WI (IOPS AF/Han), Iffa Credo) weighing from 275 to 325 grams were used. The study was performed in accordance with the EEC recommendations on animal experimentation (decree 87-848—Apr. 19, 1987). The animals were anesthetized by injection of sodium pentobarbital. The femur was approached laterally. The muscle and periosteal tissues were separated from the diaphysial shaft. A high-density polyethylene plate was fixed to the surface of the femur with Kirschner pins. A segmentary defect of 5 millimeters was implemented in the middle of the femoral diaphysis. An implant was inserted in the place of the osseous defect prior to suturing the tissues. This implant corresponds to a demineralized allogenic osseous matrix prepared from femoral diaphyses from other rats according to the procedure described by F. Blanquaert et al. (1995, *Bone*, 17: 499-506), which were impregnated or not impregnated with RGTA 1012 by incubation in a saline solution comprising 100 micrograms per milliliter of this product. The animals were then maintained in cages without ambulatory restraints. The femurs of the animals were radiographed every two weeks for 12 weeks before being euthanized. The femurs were then collected and subjected to the treatments required for histological study. The radiographs were studied especially in their densitometric aspects by image analysis.

FIG. 29 shows the effects of the RGTA on the regeneration of the long bones and shows especially the histological and radiographic studies of femurs from rats which were either treated or not treated by RGTA 1015.

FIG. 29-A shows the model defect created in the femoral diaphysis.

FIGS. 29-B, 29-D, 29-F and 29-H represent radiographs of femurs from different experimental groups. FIGS. 29-C, 29-E and 29-G represent histological sections of operative pieces corresponding to the specimens presented in 29-D, 29-F and 29-H, respectively.

FIGS. 29-C and 29-D show the femoral defect which did not receive any particular treatment. During the 12-week period there was no cicatricial phenomenon and the osseous shaft was not reconstituted.

FIGS. 29-E and 29-F show that the osseous defect was filled by the demineralized osseous matrix. In this case, filling took place but no reorganization can be seen. The structure of the filling does not present the organization of a traditional long bone.

In FIGS. 29-G and 29-H, it can be seen that the osseous defect was filled by the demineralized osseous matrix impregnated in a solution of RGTA 1015. In this case, the structure of the filling tissues corresponds to that of normal bone. The compact cortical bone is comparable to the uninjured zone in which the mark of the fixation screw can be seen. This part delimits a cavity filled with bone marrow in continuity with the original medullary cavity.

FIGS. 29-I1, 29-I2, 29-J1 and 29-J2 show the effect of RGTA 1015 on the reformation rate of the long bone. Radiographs it and 12 were taken at 8 weeks; the radiographs J1 and J2 were taken at 12 weeks. I1 and J1 correspond to the treatment presented in 29-E and 29-F in which the osseous defect was filled solely by the demineralized osseous matrix without RGTA. I2 and J2 correspond to the treatment presented in 29-G and 29-H in which the osseous defect was filled by the demineralized osseous matrix impregnated in a solution of RGTA 1015. These radiographs show an acceleration of the cicatrization and especially of the maturation of the reformed bones and in terms of a pronounced corticalization (I2 and J2) which cannot be detected in I1 and J1. RGTA 1015 acts as a regeneration agent which enables accelerated reconstitution of the osseous structure of long bone with a structure identical to that of the original bone.

Thus, in a surprising manner, RGTA 1012 impregnated in the demineralized osseous matrix, compared to a matrix impregnated in physiological serum without the polymer, induces an extremely significant acceleration in the restructuring and maturation processes of the bone. This effect is manifested in the appearance of new cortices after only 8 weeks whereas this phenomenon did not take place under the control condition. After 12 weeks, six of the seven animals treated by the association with RGTA 1012 presented in the radiological study the evidence of a complete union of the defect with the reformation of thick and delimited cortices whereas without $CM_1DS_2$ only the union is observable with radiological images of immature bone without corticalization. A quantitative image analysis study of the radiographs confirmed these observations. This study also showed that the profile of the bones treated by RGTA 1012 is comparable to that of normal bone, with the only difference being that the osseous material has a relatively low density at the experimental time point of 12 weeks. Projection of the density of the bone that is newly formed in the original defect shows that the treatment by the polymer RGTA 1012 induces a tissular restructuring via the cortical reformation and a medullary cavity.

The histological studies correlate with and confirm the results established on the basis of image analysis of the radiological data. These histological studies demonstrate the presence of new cortices constituted of compact bone with still several regions of marrow and the presence of a medullary cavity in continuity with the original diaphysial shaft, filled with new bone marrow. The femurs treated without RGTA 1012 do not show any figure of maturation. The reconstituted bone does not present any specific organization. It is constituted by a heterogeneous mixture of compact bone and medullary tissue without specific territorial delimitation.

These results illustrate the osteoinductive effects of the polymers of the invention on their capacity to induce not only the repair of the long bones but also and especially their potential to regulate the homeostasis of the regenerated tissues at the level of their mass as well as their reorganization.

The properties of the RGTA as regulatory agent of the homeostasis of the osseous tissues, i.e., of the tissular mass, its functionality and its restructuring are confirmed by Example 17 below.

EXAMPLE 17

Effects of the RGTA on the Restructuring and the Protection of the Osseous Mass in a Model of Acute Periodontal Disease in the Hamster The model used in this example pertains to the osseous restructuring of the mandible of the hamster.

Periodontal disease is induced in golden Syrian hamsters (Dépré breeding center, references HSM 41/50) after two weeks of a hyperglucidic diet. The feed administered was composed of sucrose (56%), powdered skimmed milk (28%), whole wheat flour (6%), brewer's yeast (4%), powdered alfalfa (3%), liver powder (1%) and sodium chloride (2%).

The animals were distributed into experimental groups. Fourteen animals constituted the control groups which received a normal diet comprised of dry feed. Twenty-four animals constituted the experimental groups subjected to the hyperglucidic diet. They developed chronic periodontal disease which was established at the end of two months. After this time point, the experimental groups received each week for 3 weeks an intramuscular injection of RGTA 1005 at different doses comprised between 0.1 and 15 milligrams per kilogram in a volume of 0.5 milliliters of buffered physiological serum. The control groups received an injection of physiological serum without RGTA 1005 (SHAM). The animals' weights were measured each week. One month after each type of treatment, the animals were sacrificed, the mandibles were collected and prepared for histological study. The inclusions of the operative pieces were implemented in stabilized methyl methacrylate.

In this model of periodontal disease, only 200 micrometers in height could be processed for each hemimandible. The system is standardized to always study the same sequence of sections at a depth that is defined and referenced by the osseous tissues between the roots of the two first molars of the lingual side.

The periodontal disease at the level of these molars is manifested by the appearance of a periodontal pouch which delimits a volume filled with bacterial plaque. This disease leads to a notable destruction of the periodontal bone which is characterized by a notable osteoclastic resorption and a reduction in the osseous surfaces in apposition, i.e., to an osteosynthesis phase.

The osseous resorption is quantified by measuring the zones of contact between the bone and the osteoclasts (Oc). These are giant cells that are stained blue by toluidine blue. The apposition in turn is characterized by a band of osteoid tissue, identified by an attenuated blue coloration covered by osteoblasts. In contrast to the osteoclasts, the osteoblasts are cells of small size, of cubic form and mononuclear. The quantifications of these phenomena are performed with an imaging system that uses an image-processing program.

Figure 30:
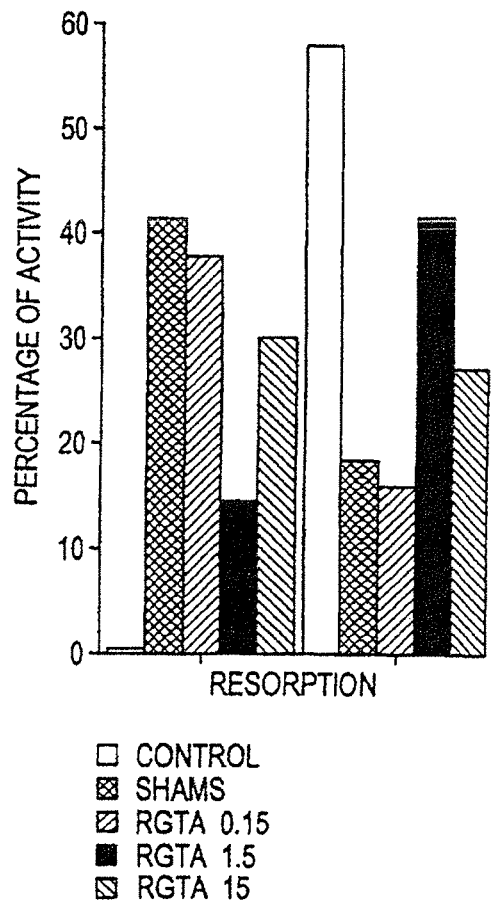
FIG. 30 is a graph showing the effects of selected polymers of the invention on the regulation of the osseous mass and on the quality of its restructuring in chronic periodontal disease.

FIG. 30 presents the quantifications obtained under the various experimental conditions. In the control animals who did not develop the disease, the resorption activity is practically nonexistent whereas the apposition activity is noteworthy. In the untreated animals (SHAM), the disease was strongly developed and characterized by an intense resorption and a low degree of apposition. In the animals treated by the $CM_1DS_2$, particularly at the dose of 1.5 milligrams per kilogram, the resorption rate is greatly diminished and is associated with a very large apposition rate which reaches close to 80% of the rate observed in the control animals.

These effects were obtained by intramuscular injection. They show that the RGTA regulate the osseous tissue mass by re-equilibrating the balance of the restructuring between resorption and apposition.

EXAMPLE 18

Pharmacokinetic Data Demonstrating the Properties of the RGTA for Vectorizing Molecules Towards Injured Tissues This example illustrates the capacity presented by the polymers of the invention for fixing themselves in a specific manner and concentrating at the level of the sites of tissular injury.

In the model of the regeneration of crushed muscle described in Example 7, a lesion is implemented on the EDL of the left paw of the animals. Each animal receives an intravenous injection of $2 \cdot 10^6$ cpm of RGTA 1012 radiolabeled with tritium by the company SibTech, Inc. (NY, USA). The specific activity of this tracer is 20 millicurie per milligram.

At different postoperative times, the injured EDL muscles of the left paws and the uninjured muscles of the right paws were collected and frozen in liquid nitrogen. The implementation of frozen histological sections enabled, by means of a beta imager (Societe Biospace), measurement of the quantity of radiolabeled product fixed at the level of the tissue sections studies. The results presented in Table V below show that the injured muscles concentrated after 24 hours a quantity of radioactive product approximately 5 times greater than the uninjured muscles the labeling level of which did not differ from the device's background noise.

TABLE V

| | cpm of RGTA 1012 fixed at the level of the tissues | | |
|---|---|---|---|
| Postoperative time | 24 hours | 48 hours | 96 hours |
| Injured muscle tissue | 11,800 ± 890 | 10,150 ± 10120 | 9000 ± 790 |
| Contralateral control muscle tissue | 2060 ± 530 | 1980 ± 390 | 1870 ± 640 |
| Background noise of registration | 1800 ± 160 | 1780 ± 210 | 1950 ± 180 |

These results demonstrate the autotargeting capacities of the polymers of the invention which concentrate themselves specifically at the level of the tissues presenting a disorder or a lesion. Thus, a particularly interesting property of these polymers resides in their capacity to vectorize a medical or diagnostic principle.

EXAMPLE 19

Effects of RGTA in Periodontics and on the Osseous Mass

In the field of periodontics, a macroscopic study of the loss of alveolar bone was performed on the periodontitis of the hamster.

After a 2-month period for induction of the disease, the animals (n=20) were treated via the IM route for an additional 2 months without acting on the initial cause of the disease, i.e., the bacterial component. Other animals were left untreated (n=20). These two groups were compared with healthy hamsters (no periodontitis) (n=12).

At the end of the experimental period, all fleshy tissues were removed from the superior maxillaries so as to enable determination of the bone loss. The zone of the first molar was photographed in a standardized manner. A reference line was traced on each photograph which corresponded to the enamel-cement junction. Then a second line was traced which ran along the contours of the osseous ridge. These two lines were reunited in front of and behind the first molar. This surface was measured.

It should be noted that in the controls, there is a zone of denudation of the root which corresponds to:
- a zone of physiological fibrous insertion which anchors the gum on the root,
- a loss of bone height which is produced in relation to the aging of the animals.

In our animals this denudation represented 0-96 mm².

In the diseased animals, the bone loss was 1.34 mm², which includes the initial physiological zone (which was destroyed over the course of the periodontitis) and a part of the loss due to aging. Nevertheless, we could conclude that the disease induced a bone loss on the order of 0.38 mm² (difference: p<0.0001).

In the treated animals, there is always an incompressible zone (the same is true of the controls). The denudation of the root represents 1.02 mm² in these animals. Thus, there is a net deficit in relation to the controls of 0.06 mm² (difference not significant) and an improvement by 0.32 mm² in relation to the untreated animals (p=0.0005).

The invention claimed is:

1. A process for tissue and cell regeneration, protection, preservation and anti-aging in vivo and ex vivo comprising administering a therapeutically effective amount of a pharmaceutical composition to a patient in need thereof, the pharmaceutical composition comprising at least one biocompatible polymer of the following general formula (I):

$$A_a X_x Y_y \quad (I)$$

wherein:
A represents a monomer,
X represents a carboxyl group bonded to monomer A and is contained within a group according to the following formula: —R—COO—R', in which R is a bond or an aliphatic hydrocarbon chain, optionally branched and/or unsaturated, and which can contain one or more aromatic rings except for benzylamine and benzylamine sulfonate, and R' represents a hydrogen atom or a cation,
Y represents a sulfate or sulfonate group bonded to monomer A and is contained within a group according to one of the following formulas: —R—O—SO₃—R', —R—N—SO₃—R', —R—SO₃—R', in which R is a bond or an aliphatic hydrocarbon chain, optionally branched and/or unsaturated, and which can contain one or more aromatic rings except for benzylamine and benzylamine sulfonate, and R' represents a hydrogen atom or a cation,
a represents the number of monomers A such that the mass of the at least one biocompatible polymer of formula (I) is greater than approximately 5,000 da,
x represents the substitution rate of the monomers A by the groups X, which is between approximately 20 and 150%, and
y represents the substitution rate of the monomers A by the groups Y, which is between approximately 30 and 150%, and
a pharmaceutically acceptable vehicle.

2. A process for treating and/or preventing aging comprising administering, to a patient in need thereof, a therapeutically effective amount of the pharmaceutical composition which comprises at least one biocompatible polymer of the following general formula (I):

$$A_a X_x Y_y \quad (I)$$

wherein:
A represents a monomer,
X represents a carboxyl group bonded to monomer A and is contained within a group according to the following formula: —R—COO—R', in which R is a bond or an aliphatic hydrocarbon chain, optionally branched and/or unsaturated, and which can contain one or more aromatic rings except for benzylamine and benzylamine sulfonate, and R' represents a hydrogen atom or a cation,
Y represents a sulfate or sulfonate group bonded to monomer A and is contained within a group according to one of the following formulas: —R—O—SO₃—R', —R—N—SO₃—R', —R—SO₃—R', in which R is a bond or an aliphatic hydrocarbon chain, optionally branched and/or unsaturated, and which can contain one or more aromatic rings except for benzylamine and benzylamine sulfonate, and R' represents a hydrogen atom or a cation, a represents the number of monomers A such that the mass of the at least one biocompatible polymer of formula (I) is greater than approximately 5,000 da, x represents the substitution rate of the monomers A by the groups X, which is between approximately 20 and 150%, and y represents the substitution rate of the monomers A by the groups Y, which is between approximately 30 and 150%, alone or in association with SOD; and a pharmaceutically acceptable vehicle.

3. A process according to claim 1 or 2, wherein R of the groups X and Y is selected from the group consisting of alkyl, allyl, aryl, linear and branched groups.

4. A process according to claim 1 or 2, wherein the monomers A, which can be identical or different, are selected from the group consisting of sugars, esters, alcohols, amino acids and nucleotides.

5. A process according to claim 1 or 2, wherein at least one monomer A is a sugar.

6. A process according to claim 1 or 2, wherein the at least one biocompatible polymer comprises at least one functional chemical group Z, which is different from X and Y, and which confers supplementary biological or physicochemical properties, wherein the at least one functional chemical group Z is conjugated to A and/or X and/or Y.

7. A process according to claim 6,
wherein the at least one functional chemical group Z comprises a plurality of functional chemical groups Z, and
wherein the rate of substitution of monomers A by the plurality of functional chemical groups Z is between approximately 0 and 50%.

8. A process according to claim 6,
wherein the at least one functional chemical group Z comprises a plurality of functional chemical groups Z, and
wherein at least one of the plurality of functional chemical groups Z is a substance which confers on the at least one biocompatible polymer additional solubility or lipophilic properties.

9. A process according to claim 8, wherein the plurality of functional chemical groups Z, which can be identical or different, are selected from the group consisting of amino acids, fatty acids, fatty alcohols, ceramides, and nucleotide addressing sequences.

10. A process according to claim 6,
wherein the at least one functional chemical group Z comprises a plurality of functional chemical groups Z, and
wherein the plurality of functional chemical groups Z, which can be identical or different, are therapeutic or diagnostic agents.

11. A process according to claim 10, wherein the at least one functional chemical group Z is selected from the group consisting of an anti-inflammatory, antimicrobial, antibiotic, enzyme and a growth factor.

12. A process according to claim 6,
wherein the at least one functional chemical group Z is covalently bonded directly to the monomer A or covalently bonded to the X and/or Y groups.

13. A process according to claim 6,
wherein the at least one functional chemical group Z is conjugated to the at least one biocompatible polymer of formula (I) by bonds other than covalent bonds.

14. A process according to claim 13,
wherein the at least one functional chemical group Z is conjugated to the at least one biocompatible polymer of formula (I) by ionic or hydrophilic interaction.

15. A process according to claim 1 or 2,
wherein the at least one biocompatible polymer comprises at least one functional chemical group Z, which is different from X and Y, and which confers supplementary biological or physiochemical properties
wherein the groups X, Y and Z are bonded directly to the monomer A, or bonded to each other with only one of them being bonded to the monomer A.

* * * * *